(12) United States Patent
Eastmond

(10) Patent No.: US 8,093,452 B2
(45) Date of Patent: Jan. 10, 2012

(54) REDUCED RDM-1 GENE EXPRESSION IN PLANTS

(75) Inventor: Peter Eastmond, Warwick (GB)

(73) Assignee: University of York, Heslington, York (GB)

( * ) Notice: Subject to any disclaimer, the term of this patent is extended or adjusted under 35 U.S.C. 154(b) by 752 days.

(21) Appl. No.: 11/952,841

(22) PCT Filed: Jun. 9, 2006

(86) PCT No.: PCT/GB2006/002117
§ 371 (c)(1),
(2), (4) Date: Jun. 10, 2008

(87) PCT Pub. No.: WO2006/131750
PCT Pub. Date: Dec. 14, 2006

(65) Prior Publication Data
US 2008/0271207 A1 Oct. 30, 2008

(30) Foreign Application Priority Data

Jun. 10, 2005 (GB) .................................. 0511810.4
Jul. 28, 2005 (GB) .................................. 0515510.6

(51) Int. Cl.
*C12N 15/87* (2006.01)
*C12N 5/14* (2006.01)

(52) U.S. Cl. ........ 800/278; 800/281; 800/285; 435/410; 435/419

(58) Field of Classification Search .................. None
See application file for complete search history.

(56) References Cited

U.S. PATENT DOCUMENTS

| | | | |
|---|---|---|---|
| 5,743,477 A | 4/1998 | Walsh et al. | |
| 2005/0182570 A1* | 8/2005 | Geourjon et al. | 702/19 |
| 2006/0107345 A1* | 5/2006 | Alexandrov et al. | 800/278 |

FOREIGN PATENT DOCUMENTS

| | | |
|---|---|---|
| EP | 1 033 405 | 9/2000 |
| WO | WO-03/106670 | 12/2003 |
| WO | WO-2004/113543 | 12/2004 |

OTHER PUBLICATIONS

Database UniProt_201006, Accession No. Q9LZA6, Oct. 1, 2000.*
Database EMBL, "*Arabidopsis thaliana* putative protein (At5g04040) mRNA, complete CDs," Database Accession No. AY136470 (2002).
Eastmond, "Cloning and Characterization of the Acid Lipase from Castor Beans," *J. Biol. Chem.*, 279(44):45540-45545 (2004).
Eastmond, "Sugar-Dependent1 Encodes a Patatin Domain Triacylglycerol Lipase That Initiates Storage Oil Breakdown in Germinating *Arabidopsis* Seeds," *The Plant Cell*, 18:665-675 (2006).
Karim et al., "Identification and Characterization of a Triacylglycerol Lipase in *Arabidopsis* Homologous to Mammalian Acid Lipase," *FEBS Lett.*, 579:6067-6073 (2005).
Matsui et al., "A Tomatao lipase homologous to DAD1 (*LeLID1*) is Induced in Post-Germinative Growing Stage and Encodes a Triacylglycerol Lipase," *FEBS Lett.*, 569:195-200 (2004).
Mignery et al., "Molecular Characterization of the Patatin Multigene Family of Potato," *Gene*, 62:27-44 (1988).
Great Britian Search Report for Application No. GB0511810.4, dated Sep. 29, 2005.
International Preliminary Report on Patentability for International Application No. PCT/GB2006/002117, dated Dec. 11, 2007.
International Search Report for International Application No. PCT/GB2006/002117, dated Jun. 13, 2007.
Written Opinion for International Application No. PCT/GB2006/002117, dated Jun. 13, 2007.

* cited by examiner

*Primary Examiner* — Eileen B O Hara
(74) *Attorney, Agent, or Firm* — Marshall, Gerstein & Borun LLP

(57) ABSTRACT

We describe a plant lipase polypeptide and nucleic acids that encode said polypeptide which has homology to a patatin and which has phospholipase and/or triacylglycerol lipase activity.

15 Claims, 12 Drawing Sheets

Figure 1a

```
ATGGATATAAGTAATGAGGCTAGTGTCGATCCCTTTTCGATTGGACCATCATCTATCATGGGTCGAACCA
TTGCTTTCAGAGTCTTGTTCTGTAGATCAATGTCACAGCTTAGGCGTGATCTCTTTCGGTTCTTGTTGCA
TTGGTTTCTTAGATTTAAGCTGACCGTTTCACCGTTTGTGTCGTGGTTTCATCCTCGGAACCCTCAAGGG
ATTTTAGCGGTGGTTACAATCATTGCCTTTGTGTTGAAACGATACACGAATGTGAAAATAAAGGCGGAAA
TGGCTTACCGGAGGAAGTTTTGGAGGAATATGATGCGGACGGCTTTGACTTATGAGGAATGGGCTCATGC
TGCTAAGATGTTAGAGAAGGAAACACCAAAGATGAATGAATCTGATCTTTATGATGAAGAGTTGGTTAAG
AACAAGCTTCAGGAGCTTCGTCATCGTCGCCAAGAAGGCTCACTTAGAGACATTATGTTTTGTATGAGAG
CTGATTTGGTGAGGAATCTCGGTAATATGTGTAATTCGGAGCTTCATAAAGGTAGACTTCAGGTTCCTAG
ACATATCAAAGAGTACATTGATGAGGTGTCTACTCAGTTGAGAATGGTTTGTAACTCTGATTCAGAGGAG
CTTTCTTTAGAAGAGAAGCTTTCTTTTATGCATGAAACACGGCATGCCTTTGGTAGAACGGCTTTGCTTT
TGAGTGGTGGGCTTCTCTTGGTGCGTTTCATGTTGGTGTGGTTAGGACTTTGGTTGAGCATAAGCTTTT
ACCTCGAATAATTGCTGGTTCTAGTGTTGGATCCATCATTTGTGCTGTTGTGGCCTCAAGGTCTTGGCCA
GAACTACAGAGTTTCTTTGAGAATTCTTTGCATTCTTTACAGTTCTTTGATCAGCTCGGAGGCGTGTTCT
CAATAGTGAAACGGGTAATGACACAAGGGGCTCTACACGATATCAGACAGTTGCAATGTATGCTTAGAAA
CCTCACAAGCAATCTCACATTCCAAGAAGCTTATGACATGACAGGAAGGATTCTCGGGATCACCGTTTGC
TCCCCAAGAAAGCATGAACCTCCTCGGTGTCTTAACTATTTGACTTCGCCTCATGTGGTTATATGGAGCG
CAGTGACTGCTTCTTGTGCTTTTCCTGGTCTCTTTGAAGCTCAAGAGCTAATGGCTAAAGATCGAAGTGG
AGAGATCGTACCGTATCATCCACCTTTCAATTTGGATCCAGAAGTAGGCACTAAATCATCATCTGGACGC
CGGTGGAGAGATGGTAGTTTGGAGGTTGATTTACCAATGATGCAGCTTAAAGAACTGTTCAATGTCAATC
ATTTTATTGTGAGCCAAGCCAATCCTCACATTGCTCCATTACTGCGTCTAAAGGATTTAGTTCGAGCTTA
TGGTGGTAGATTCGCAGCTAAGCTCGCGCATCTAGTGGAGATGGAGGTCAAACATAGATGCAACCAGGTA
TTAGAGCTCGGTTTTCCTCTCGGTGGACTCGCAAAGCTTTTTGCTCAGGAGTGGGAAGGTGATGTTACAG
TTGTAATGCCTGCTACTCTTGCTCAGTACTCGAAGATTATACAAAATCCGACTCATGTCGAGCTTCAGAA
AGCGGCTAACCAAGGAAGAAGATGCACTTGGGAGAAGCTCTCAGCCATAAAATCAAACTGCGGGATCGAG
CTTGCGCTTGATGATTCTGTAGCTATTCTTAACCATATGCGGAGGCTCAAGAAAAGTGCGGAGAGAGCCG
CCACTGCCACGTCTTCGTCTCATCACGGATTGGCTTCAACCACCAGATTCAATGCTTCAAGAAGAATCCC
ATCTTGGAACGTCCTTGCCAGAGAGAACTCAACAGGCTCACTGGATGATCTAGTCACTGACAATAACCTC
CACGCTTCTTCGGGCAGGAATTTAAGCGACAGTGAAACAGAGAGCGTGGAGTTGAGTTCTTGGACAAGAA
CTGGTGGACCTTTAATGAGAACAGCTTCTGCTAATAAGTTCATTGATTTTGTTCAGAGTCTTGATATCGA
CATTGCATTGGTCAGAGGATTTAGTAGCAGTCCCAATTCTCCAGCAGTTCCTCCTGGTGGCTCGTTTACT
CCAAGCCCGAGATCCATAGCGGCTCATTCGGATATCGAATCAAACAGCAATAGCAACAATCTTGGAACAA
GCACTTCAAGCATAACAGTTACTGAAGGTGATCTTCTACAGCCTGAGAGAACGAGTAACGGATTTGTGTT
AAACGTCGTTAAAAGAGAGAACTTGGGAATGCCATCGATTGGGAACCAAAATACAGAGTTACCAGAGAGT
GTACAGCTCGATATACCGGAGAAGGAGATGGATTGTAGCTCTGTATCAGAACACGAAGAAGATGATAACG
ACAATGAAGAAGAACATAACGGCTCGAGTCTGGTTACTGTTTCTTCAGAAGATTCCGGTTTACAAGAACC
GGTGTCTGGTAGTGTTATAGATGCTTAG
```

Figure 1b

```
HVGVVRTLVEHKLLPRIIAGSSVGSIICAVVASRSWPELQSFFENSLHSLQFFDQLGGVFSIVKRVMTQGA
LHDIRQLQCMLRNLTSNLTFQEAYDMTGRILGITVCSPRKHEPPRCLNYLTSPHVVIWSAVTASCAFPGLF
```

Figure 2

MDISNEASVDPFSIGPSSIMGRTIAFRVLFCRSMSQLRRDLFRFLLHWFLRFKLTVSPFVSWFHPRNPQGI
LAVVTIIAFVLKRYTNVKIKAEMAYRRKFWRNMMRTALTYEEWAHAAKMLEKETPKMNESDLYDEELVKNK
LQELRHRRQEGSLRDIMFCMRADLVRNLGNMCNSELHKGRLQVPRHIKEYIDEVSTQLRMVCNSDSEELSL
EEKLSFMHETRHAFGRTALLLSGGASLGAF<u>HVGVVRTLVEHKLLPRI</u>IAGSSVGSI<u>ICAVVASRSWPELQS
FFENSLHSLQFFDQLGGVFSIVKRVMTQGALHDIRQLQCMLRNLTSNLTFQEAYDMTGRILGITVCSPRKH
EPPRCLNYLTS</u>PHVVIWSAVTASCAFPGLFEAQELMAKDRSGEIVPYHPPFNLDPEVGTKSSSGRRWRDGS
LEVDLPMMQLKELFNVNHFIVSQANPHIAPLLRLKDLVRAYGGRFAAKLAHLVEMEVKHRCNQVLELGFPL
GGLAKLFAQEWEGDVTVVMPATLAQYSKIIQNPTHVELQKAANQGRRCTWEKLSAIKSNCGIELALDDSVA
ILNHMRRLKKSAERAATATSSSHHGLASTTRFNASRRIPSWNVLARENSTGSLDDLVTDNNLHASSGRNLS
DSETESVELSSWTRTGGPLMRTASANKFIDFVQSLDIDIALVRGFSSSPNSPAVPPGGSFTPSPRSIAAHS
DIESNSNSNNLGTSTSSITVTEGDLLQPERTSNGFVLNVVKRENLGMPSIGNQNTELPESVQLDIPEKEMD
CSSVSEHEEDDNDNEEEHNGSSLVTVSSEDSGLQEPVSGSVIDA

Figure 3a

```
CTAAAGCCATGGATGATGCTGGTAAAATCACTTCCACAAGCCATCTCATAGTGAGCCCAGATGAAGGAAC
CTTTTTGGACCTGTTCAAGCACATTGTGCTGAGTGATTTGGGCAGTGGAGCCAAATTCTTTAGGGCTTCA
GATCAGAGAGTGCCTGCTACGGCAGCATATTATAGCAGGTGGCCTGTTTCAGTTTTCATTTGCAAAATAC
TTCAACTTTTCCAGATGCCAGCCGCGATGCTTGGTCATCTTACTGATTTCTTGCTCAACTTCTATTATCA
GAATCATGGCTTCCTTGGCATACTCAGAAACATCTTCTTAATAAGACTGAAGATACCAAAAAGAGGTGAA
GCCGACTTTATAAGCACGATAGGGTATTTAGATTCACGAATGGACCTTCACGGGACGCCAATGGTGTCGC
ACCAGGCAGACGAAGTGATTTCAAATGCAGATAATCCAAGCCTGAAAGAAGGGCACAATTCAAAGATAAA
AGGAGCCCTTGGGAACCGATCTCTCATGGATCTTTGTATCATGGCGTCAAAGCTTGCTTATGAAAATACC
AAAGTTGTTGAAAGAGTAGTTGCCGAACATTGGAAGATGCATTTCGTGGCTGACTATGGGGCATGAATT
ATTTCCAAGATGCAAGGAACACTCATGCGTTCATCTTTTGTGACAAGCCAAAAGATGCAAACTTGATAGT
GATCAGCTTCAGAGGCACAGGACCTTTTAGTATACCAAATTGGTGTACTGATTTTGATTTCTCCTTAGTT
GGGTTGGGAGACGCAGGAAGTGTCCATGTTGGATTCTTAGAAGCAATGGGTTTGGGTCACAGAAATTCTA
TTTCCAGCTTTGAGACTAGCATTAACACAAAGTCGCCAGGAAGCATAACCGAATTAAGGAAAGAGTCCGA
GATGGCTCCGGACCACTTGGTATGGGCATATGATGGTGTTTACTTTCTTGCGGCATCGACGCTCAAGGGA
TTACTAAAAGACCACAAGAACGCAAAATTTGTAGTCACTGGGCATAGCTTAGGTGGTGCACTTGCTATAC
TGTTCACATGCATTCTTGAGATACAGCAGGAGACAGAGGTGCTTGACAGACTGCTAAATGTATACACATT
CGGACAGCCTAGGATTGGGAACTATAATCTTGGTTACTTCATGCAGAACCGTCTCAATTTTCCAGAACGT
AGGTATTTCAGGGTGGTTTACTGCAATGACATGGTTCCTAGGGTGCCTTTCGATGATGTCTTCTTCACTT
TCGAGCATTTCGGAACCTGCATTTACTATGATAGCCGCTTCTTTGGCTACTTTACCAAAGAGGAGCCCAG
CAGAAACCCTTTCGGAATAGAAAATGCCATCAGTGCGCACATCACCGCCTGGTGGGAGCTCTGGAGAAGT
TTCATATTAAATCACGTATATGGCGCAGAATACAAGGAGACCTGGGAATCCAGAATGTTCAGGATATTGG
GACTGTTTCTCCCTGGTGTTGCAGCTCATAGTCCTGTGAATTATGTCAATTCTGTCAGGCTTGGAAGGGA
GCTTGCAATTCCCTTGATGTCTCTGAAAATGATGGCACAAGGTTACTAGAATTATCGTTATAAAGTCTAA
GAGATGATCATTAATGATAAATGGTTCACTCTTTGCCAAAAAAAGAAAAATAATCAAAAGGCTTACGCTA
TTGTAATAAAAGGATAGCTGTTTCATGAACAGGTCGCCTAGGGTTGTGGTGTGGAGCTTTGATATGCATA
TATGCATATATGGCCTGTTTGTTTGTCAGTTTGTTTTTCTCTTTAAACAAAATGAAATGCGGTAGTTCAA
TAAAAAGGAACGTTGAGTAGTTTTTGGGTTGCCAAAAAAAAAAAAAAAA
```

Figure 3b
```
MDDAGKITSTSHLIVSPDEGTFLDLFKHIVLSDLGSGAKFFRASDQRVPATAAYYSRWPVSVFICKILQL
FQMPAAMLGHLTDFLLNFYYQNHGFLGILRNIFLIRLKIPKRGEADFISTIGYLDSRMDLHGTPMVSHQA
DEVISNADNPSLKEGHNSKIKGALGNRSLMDLCIMASKLAYENTKVVERVVAEHWKMHFVADYGGMNYFQ
DARNTHAFIFCDKPKDANLIVISFRGTGPFSIPNWCTDFDFSLVGLGDAGSVHVGFLEAMGLGHRNSISS
FETSINTKSPGSITELRKESEMAPDHLVWAYDGVYFLAASTLKGLLKDHKNAKFVVTGHSLGGALAILFT
CILEIQQETEVLDRLLNVYTFGQPRIGNYNLGYFMQNRLNFPERRYFRVVYCNDMVPRVPFDDVFFTFEH
FGTCIYYDSRFFGYFTKEEPSRNPFGIENAISAHITAWWELWRSFILNHVYGAEYKETWESRMFRILGLF
LPGVAAHSPVNYVNSVRLGRELAIPLMSLKMMAQGY
```

Figure 4a

```
GATCTTCAAAGTAGTTTTGAACTCTCTGCTGAGGGAAAAAAAGAGTGAGGGAAGTGAGAAACCAAAAGCC
ATGGCTGCTTCTGCTACTACTAGCAATAATATTGCTCCAAACTTCTTGGTTGTTGACCCAAAAAAGGGAA
GAAAAAGAGACATATTCAAGTATTTGGTGAGGAAAGATGTGAAGAGTGGAATGAGTTTCTTGGATAGTTC
AGAGGAAGGAGTTAAAGGTGGCGCAGCAGTTGATCATAGGTGGATTTTATTGGTTTCTATCATCATTCGG
AGGGTTCTTGCGCTTATTGATACCCCATTAAAGTACCTTGGATATGTCATTGATTTCTTTCTCAACCTTA
TCTCCCAAAATAGTGGATTCTCTGGCATACTCAACAACTTTCTCCATGGAAACCTGAAGATACCGAGGAG
AGGAACAGAGAATTTTATAAGCACGATTGGGCAATTGGATGGGCGAATAGACCTTTATAGAACTACAATA
TTATCGGAGAAAGTAGATGATTCTGTTGCTACTGATGTTAACAACATTAAAGCAGAACTGGGTAATCGAT
ATCTCATGGATCTTTGTATCATGGCAGCCAAACTTGTCTATGAGAATGAGAAAGTTGCTCAAAATGTTGT
TGATCGTCACTGGAAGATGCATTTTGTGGCTTTCTACAACTGCTGGAATGAGTACCAAAAGCAAACAAC
ACCCAAGTGTTCATATGTTGTGACAAGCCAAAGGATGCAAATTTGATAGTGGTCAGCTTTAGAGGAACAG
AACCATTTAATGCACAAGATTGGAGTACGGATTTTGATTTCTCGTGGTATGAAATCCCAAAAGTTGGAAA
GATCCATATTGGATTCTTAGAAGCTTTAGGTCTGGGCAACAGAAGTGACGCTACCACTTTCCAAACTCAC
CTTCAGAGGAAACATACAGGTTTCTTCCATCTAAATGGTGAGTCTGAAGGCAATATGACGGAATGGGCAA
AGAAGAGTGCATACTATGCTGTCGCGTTGAAGCTAAAGAGCTTACTGAAAGAACACAGGAATGCTAAATT
TATAGTCACTGGACATAGTTTAGGTGGAGCACTTGCAATATTGTTCCCGTCAATACTGGTTATACAGGAG
GAGACAGAGATGCTAAACAGGTTGCTGAACATATACACATTTGGGCAGCCAAGAATTGGAGATGCACAGC
TTGGAACTTTCATGGAGTCCCACTTGAATTATCCAGTTACTAGATACTTCAGGGTTGTTTACTGCAACGA
TATGGTGCCTAGAGTGCCTTTCGATGACAAGATTTTCGCTTTCAAGCATTTCGGTACATGTCTTTACTAT
GATAGCCGCTACTTTGGCCGATTTATGGATGAGGAGCCGAACAGAAATTATTTTGGACTGAGACACATAA
TTCCAATGCGGGTGAATGCATTATGGGAACTATTCAGAAGTTTTATGATAACCCATGCACATGGACCTGA
CTACCAGGAGAGTTGGTTCTGCACTCTTTCCAGGGTAGCAGGACTGGTGCTTCCTGGTGTTGCTGCTCAT
AGTCCTATAGATTATGTTAATTCAGTTAGGCTTGGAAAGGAGAGAGTAGCTCCAATGACATCCTTGAAAA
GCTTCGCTCGCAAGTCATAAATCTGGGTTGCACTTGTACTCTTCTTCATGGATGAGACACTGAACACAAA
GGAAAATAATAACAGGGTGCAGTTTAAAATGATCATAAGGGAAATAAATCTTATATTTCTTACTCTTACG
GAAATTTGATAATCTGTGACCTTGTGGTTGTGGGTAGTTCCAATTTAATTTCTTTTTCTTTTCAATAAAA
ATCCTGTACTTCGGTGATAATATGAATTATAGTGTGACTTTTTTGGTTGCCCATAGAAAAAAAAAAAAAA
AAAAAAAAA
```

Figure 4b

```
MAASATTSNNIAPNFLVVDPKKGRKRDIFKYLVRKDVKSGMSFLDSSEEGVKGGAAVDHRWILLVSIIIR
RVLALIDTPLKYLGYVIDFFLNLISQNSGFSGILNNFLHGNLKIPRRGTENFISTIGQLDGRIDLYRTTI
LSEKVDDSVATDVNNIKAELGNRYLMDLCIMAAKLVYENEKVAQNVVDRHWKMHFVAFYNCWNEYQKQNN
TQVFICCDKPKDANLIVVSFRGTEPFNAQDWSTDFDFSWYEIPKVGKIHIGFLEALGLGNRSDATTFQTH
LQRKHTGFFHLNGESEGNMTEWAKKSAYYAVALKLKSLLKEHRNAKFIVTGHSLGGALAILFPSILVIQE
ETEMLNRLLNIYTFGQPRIGDAQLGTFMESHLNYPVTRYFRVVYCNDMVPRVPFDDKIFAFKHFGTCLYY
DSRYFGRFMDEEPNRNYFGLRHIIPMRVNALWELFRSFMITHAHGPDYQESWFCTLSRVAGLVLPGVAAH
SPIDYVNSVRLGKERVAPMTSLKSFARKS
```

Figure 5

```
Query:  243  FHVGVVRTLVEHKL----LPRIIAGSSVGSIICAVVAS----RSWPELQSFFENSLHSLQ  294
Sbjct:   12  AHIGVLKALEEAGIRLLDYFDVIAGTSAGAIVAALLATGRDPNRPEELEEFYLE--VKKR   69

Query:  295  FFDQLGGVFSIVKRVMTQGALHDIRQLQCMLRNLTSNLTFQEAYDMTGRILGITVCSPRK  354
Sbjct:   70  IFLDSSPKLDLTGPSL--GGLYDGDRLEKLLKEALGDLLLEDLW----KPLVIPATDLST  123

Query:  355  HEPPRCLNYLTSPHVVIWSAVTASCAFPGLFEAQEL  390
Sbjct:  124  GEPVIFRLNSDPSDGDLWDAIRASSAAPGYFPPVPI  159
```

Figure 6A (RDM1 protein and cDNA showing mutation sites)

```
RDM1
MDISNEASVDPFSIGPSSIMGRTIAFRVLFCRSMSQLRRDLFRFLLHWFLRFKLTVSPFVSWFHPRNPQGI
LAVVTIIAFVLKRYTNVKIKAEMAYRRKFWRNMMRTALTYEEWAHAAKMLEKETPKMNESDLYDEELVKNK
LQELRHRRQEGSLRDIMFCMRADLVRNLGNMCNSELHKGRLQVPRHIKEYIDEVSTQLRMVCNSDSEELSL
EEKLSFMHETRHAFGRTALLLSGGASLGAFHVGVVRTLVEHKLLPRIIAGSSVGSIICAVVASRSWPELQS
                              D (rdm1-3)
FFENSLHSLQFFDQLGGVFSIVKRVMTQGALHDIRQLQCMLRNLTSNLTFQEAYDMTGRILGITVCSPRKH
EPPRCLNYLTSPHVVIWSAVTASCAFPGLFEAQELMAKDRSGEIVPYHPPFNLDPEVGTKSSSGRRWRDGS
LEVDLPMMQLKELFNVNHFIVSQANPHIAPLLRLKDLVRAYGGRFAAKLAHLVEMEVKHRCNQVLELGFPL
          K (rdm1-1)       S (rdm1-2)
GGLAKLFAQEWEGDVTVVMPATLAQYSKIIQNPTHVELQKAANQGRRCTWEKLSAIKSNCGIELALDDSVA
ILNHMRRLKKSAERAATATSSSHHGLASTTRFNASRRIPSWNVLARENSTGSLDDLVTDNNLHASSGRNLS
DSETESVELSSWTRTGGPLMRTASANKFIDFVQSLDIDIALVRGFSSSPNSPAVPPGGSFTPSPRSIAAHS
DIESNSNSNNLGTSTSSITVTEGDLLQPERTSNGFVLNVVKRENLGMPSIGNQNTELPESVQLDIPEKEMD
CSSVSEHEEDDNDNEEEHNGSSLVTVSSEDSGLQEPVSGSVIDA RDM1
ATGGATATAAGTAATGAGGCTAGTGTCGATCCCTTTTCGATTGGACCATCATCTATCATGGGTCGAACCA
TTGCTTTCAGAGTCTTGTTCTGTAGATCAATGTCACAGCTTAGGCGTGATCTCTTTCGGTTCTTGTTGCA
TTGGTTTCTTAGATTTAAGCTGACCGTTTCACCGTTTGTGTCGTGGTTTCATCCTCGGAACCCTCAAGGG
ATTTTAGCGGTGGTTACAATCATTGCCTTTGTGTTGAAACGATACACGAATGTGAAAATAAAGGCGGAAA
TGGCTTACCGGAGGAAGTTTTGGAGGAATATGATGCGGACGGCTTTGACTTATGAGGAATGGGCTCATGC
TGCTAAGATGTTAGAGAAGGAAACACCAAAGATGAATGAATCTGATCTTTATGATGAAGAGTTGGTTAAG
AACAAGCTTCAGGAGCTTCGTCATCGTCGCCAAGAAGGCTCACTTAGAGACATTATGTTTTGTATGAGAG
CTGATTTGGTGAGGAATCTCGGTAATATGTGTAATTCGGAGCTTCATAAAGGTAGACTTCAGGTTCCTAG
ACATATCAAAGAGTACATTGATGAGGTGTCTACTCAGTTGAGAATGGTTTGTAACTCTGATTCAGAGGAG
CTTTCTTTAGAAGAGAAGCTTTCTTTTATGCATGAAACACGGCATGCCTTTGGTAGAACGGCTTTGCTTT
TGAGTGGTGGGGCTTCTCTTGGTGCGTTTCATGTTGGTGTGGTTAGGACTTTGGTTGAGCATAAGCTTTT
             A (rdm1-3)
ACCTCGAATAATTGCTGGTTCTAGTGTTGGATCCATCATTTGTGCTGTTGTGGCCTCAAGGTCTTGGCCA
GAACTACAGAGTTTCTTTGAGAATTCTTTGCATTCTTTACAGTTCTTTGATCAGCTCGGAGGCGTGTTCT
CAATAGTGAAACGGGTAATGACACAAGGGGCTCTACACGATATCAGACAGTTGCAATGTATGCTTAGAAA
CCTCACAAGCAATCTCACATTCCAAGAAGCTTATGACATGACAGGAAGGATTCTCGGGATCACCGTTTGC
TCCCCAAGAAAGCATGAACCTCCTCGGTGTCTTAACTATTTGACTTCGCCTCATGTGGTTATATGGAGCG
CAGTGACTGCTTCTTGTGCTTTTCCTGGTCTCTTTGAAGCTCAAGAGCTAATGGCTAAAGATCGAAGTGG
AGAGATCGTACCGTATCATCCACCTTTCAATTTGGATCCAGAAGTAGGCACTAAATCATCATCTGGACGC
CGGTGGAGAGATGGTAGTTTGGAGGTTGATTTACCAATGATGCAGCTTAAAGAACTGTTCAATGTCAATC
                              A (rdm1-1)
ATTTTATTGTGAGCCAAGCCAATCCTCACATTGCTCCATTACTGCGTCTAAAGGATTTAGTTCGAGCTTA
        T (rdm1-2)
TGGTGGTAGATTCGCAGCTAAGCTCGCGCATCTAGTGGAGATGGAGGTCAAACATAGATGCAACCAGGTA
TTAGAGCTCGGTTTTCCTCTCGGTGGACTCGCAAAGCTTTTTGCTCAGGAGTGGGAAGGTGATGTTACAG
TTGTAATGCCTGCTACTCTTGCTCAGTACTCGAAGATTATACAAAATCCGACTCATGTCGAGCTTCAGAA
AGCGGCTAACCAAGGAAGAAGATGCACTTGGGAGAAGCTCTCAGCCATAAAATCAAACTGCGGGATCGAG
CTTGCGCTTGATGATTCTGTAGCTATTCTTAACCATATGCGGAGGCTCAAGAAAGTGCGGAGAGAGCCG
CCACTGCCACGTCTTCGTCTCATCACGGATTGGCTTCAACCACCAGATTCAATGCTTCAAGAAGAATCCC
ATCTTGGAACGTCCTTGCCAGAGAGAACTCAACAGGCTCACTGGATGATCTAGTCACTGACAATAACCTC
CACGCTTCTTCGGGCAGGAATTTAAGCGACAGTGAAACAGAGAGCGTGGAGTTGAGTTCTTGGACAAGAA
CTGGTGGACCTTTAATGAGAACAGCTTCTGCTAATAAGTTCATTGATTTTGTTCAGAGTCTTGATATCGA
CATTGCATTGGTCAGAGGATTTAGTAGCAGTCCCAATTCTCCAGCAGTTCCTCCTGGTGGCTCGTTTACT
```

6A

Figure 6B

```
CCAAGCCCGAGATCCATAGCGGCTCATTCGGATATCGAATCAAACAGCAATAGCAACAATCTTGGAACAA
GCACTTCAAGCATAACAGTTACTGAAGGTGATCTTCTACAGCCTGAGAGAACGAGTAACGGATTTGTGTT
AAACGTCGTTAAAAGAGAGAACTTGGGAATGCCATCGATTGGGAACCAAAATACAGAGTTACCAGAGAGT
GTACAGCTCGATATACCGGAGAAGGAGATGGATTGTAGCTCTGTATCAGAACACGAAGAAGATGATAACG
ACAATGAAGAAGAACATAACGGCTCGAGTCTGGTTACTGTTTCTTCAGAAGATTCCGGTTTACAAGAACC
GGTGTCTGGTAGTGTTATAGATGCTTAG
```

Figure 7

```
Query: 110  TYEEWAHAAKMLEKETP----KMN---------ESDLYDEELVKNKLQELRHRRQEGSLRD 157
             TY+ W  A ++++ T    + N         S +    +++N L+E ++    +
Sbjct: 79   TYQMWCQQASVVDEITGANLWRRNFFSRRYDFNSVIEQYSILENMLREEKYDVVKEKFST 138

Query: 158  IMFCMRADLVRNLGNMCNSELH-KGRLQVPRHIKEYIDEVSTQLRMVCNXXXXXXXXXXX 216
              CM    +RN  + + +L K +      I++Y+ +   L ++ N
Sbjct: 139  TGPCM----LRNFAGIGDKKLFTKSLMGTKLLIEQYLTRILEGLDILNNQTLTPTS---- 190

Query: 217  XXFMHETRHAFGRTXXXXXXXXXXXXFHVGVVRTLVEHKLLPRIIAGSSVGSIICAVVAS 276
              F   + + G T            FH+GV+R L+    L+P II+GSS+G+ + ++
Sbjct: 191  --FFQRCKLSLGTTALILQGGSLFGLFHLGVIRGLLLQDLMPNIISGSSMGACVASLFGC 248

Query: 277  RSWPELQSFF--ENSLHSLQF-----------FDQLGGVFSIVKRVMTQGALHDIRQ-L 321
             S  +L+    +N L+ ++            +Q  +  ++++ ++  G   D+    +
Sbjct: 249  LSNEQLKQLLTDDNLLNIIKNDVDLLKSCGYGNLEQHLNLGTLIQNLIHHGYSQDVYLFI 308

Query: 322  QCMLRNLTSNLTFQEAYDMTGRILGITVCSPRKHEPPRCLNYLTSPHVVIWSAVTASCAF 381
              + +++ +    TF+E Y +TG++  I + P    P   LNY+T+P+V+I  SA+  S
Sbjct: 309  RFVMKYIVKEKTFEEVYQITGKVFNIVI-HPTDKSCPNLLNYVTTPNVLIKSAIECSLGS 367

Query: 382  PGLFEAQELMAKDRSGEIVPYHPPFNLDPEVGTKSSSGRRWRDGSLEVDLPMMQLKELFN 441
             + E   L+ K+   EI P+   N++    K +      + S+ + P +L ELFN
Sbjct: 368  GVISEDTSLLCKNLENEIEPF---LNINKNKQVKFLTPENANNPSI-TESPYTRLTELFN 423

Query: 442  VNHFIVSQANPHIAPLL 458
            VN+FIVS A P++APL+
Sbjct: 424  VNNFIVSLARPYLAPLV 440

Query: 474  KLAHLVEMEVKHRCNQVLELGFPLGGLAKLFAQEWEG----DVTVVMPATLAQYSKIIQN 529
            KL ++  ME +HR + LG    + +L  E      ++ VV         ++II+
Sbjct: 540  KLKNIATMEFRHRMEVLDNLGLLCSLIKRLIIDEKTPRSATEIAVVPRMKSLSLTRIIEG 599

Query: 530  PTHVELQKAANQGRRCTWEKLSAIKSNCGIELALDDSV 567
             +  +         G R TW  L+ IK+ C +E  LDD +
Sbjct: 600  QLN-NIPYWIKSGERSTWPALALIKTRCAVEFKLDDII 636
```

Figure 9A aggttgatttaccaatgatgcaattgaaggaactgttcaacgtcaatcactttattgtga
gtcaggcaaatcctcatattgctccgttgttgagaatgaaggagtttgtgagagcttatg
gtggtaattttgctgccaagcttgctcatctcactgagatggaagtaaagcatagatgca
atcaggtactggaacttggttttccattaggaggacttgccaagcttttgctcaagaat
gggagggcgatgtcactgttgttatgcctgccacagtgtctcagtacttgaaaataattc
aaaatccaactcacatggaacttcaaaaggcagccaaccaagggagaagatgcacttggg
agaagct

Figure 9B

VDLPMMQLKELFNVNHFIVSQANPHIAPLLRMKEFVRAYGGNFAAKLAHLTEMEVKHRCN
QVLELGFPLGGLAKLFAQEWEGDVTVVMPATVSQYLKIIQNPTHMELQKAANQGRRCTWE
K

Figure 10A
atggatataagcaacgaagcaggcgttgatgcgttctcaattataggacccacgactata
atcggaagaacaattgccgtccggatcttgttctgcaactccgtgtctatattcagacac
aaagttttcagaattctcaattttcctcagaggaggtagggttttactatccgttt
gtgtccttgctacatccaggaatccacaagggatattagtaatggtgacgacgatggcc
tttctgttgaaccgctacacaagcttaaaagcaaaggctgagatggcttacaggagaaaa
ttttggaggaacatgatgagagctgcattgacatatgaggaatggtctcacgccgcaaag
atgctagataaagagactcccaaggtgaacgagacagatcttttgatgtggagctcgta
agtaataagcttgatgaacttaagcatagacgtcatgagggctctcttagagacattat
ttctgtatgagagctgatcttgtgagaaatctcggtaatatgtgtaaccctgagcttcac
aagggaaggcttcacgtgccgagactcatcaaagagtatatcgatgaggtctctacacag
cttaggatggtttgcgacatggacactgaagagctttctctggaggagaaactttcttt
atgcatgagaccagacacgcgtatggaagaacagctctacttctcagtggaggagcttct
cttggggctttccatcttggtgtggtcaagacgcttgtggaacataagctattgccaaga
attatagctggttcaagcgtggggtctgtaatgtgtgcggttgtgggacaaggtcatgg
cccgagttgcagagcttctttgaagggcctggcatgctctgcagttctttgatcagatg
ggaggaattttcactactgtgaagcgggttatgactcaaggcgcagtccatgagatccgg
catctgcaatggaagttgaggaatctcaccaacaatctcacattccaagaagcttacgac
ataacaggacggattctagggataacagtttgttccctgaggaaacacgagccgcctaga
tgtctcaattatctgacttcgcctcatgttgtgatatggagtgcagtgactgcatcttgt
gctttcccaggtcttttcgaagctcaagaactcatggccaaagacagaactggagagatt
gttccttatcatccaccatttaacttagatcctgaagagggctcagcatcagttcggcgc
tggagggacggtagtttggagatggacttaccgatgatacaactcaaagagcttttcaat
gtcaaccatttcattgtcagtcaagccaaccctcacatagcacccttcttgaggatgaag
gagtttgtgagagcttgtggaggtcgatttgcagcaaagctcgcgcaactcgcggagatg
gaagtgaagcatagatgtaatcaagtactagaactcgggcttcctctaagagaagtagct
tcactatttgctcaagaatgggaaggcgatgtcacaattgtcatgccagctactttttct
cagtacttgaagatcatacaaaatccaagcaatgtagagattcaaaaggcagcaaatcaa
ggaaggagatgcacctgggaaaaactagcagtaatcaaagcaaacttcgggatcgaacta
gcactcgacgagtgcgtcaccgttcttaaccacatgcgccgccttaaacgcagcgcagaa
agagccgctgctttctccgccatctcttcctctccaccatctaaacatcttttggccgga
accaatagattcaacgcctccaaaagaatcccttcctggaattgtatagctcgtcagaac
tcctccggatccgtcgatgatgatgtcctagctgaagcttcacggttgtaccagcatatc
gtggttggatctggggaggaatagtaatcgaaccagtaacttaagccatacctatgacgca
ggaagcgaatgtgattctccagaagctgaagattggactagatctggcggaccattgatg
aggaccaattctgctcagatgttcactgactacgtccagaatctcgacgccgttgatccg
gaacagattagagcttcggagaacgattcgattgtagctgcttcgtcgtcttctcatagc
atcactgtcacggaaggcgattatcttcagacgggaagaacacacaatggatttgtgttg
aatctcgttagaggagagaattttgaggatgaattcagagccggaagatagccaaaacgaa
agtgaaattccggagactccggaaagcgtgcaacttgattcgccggaaaaggacattatt
gacggagagagctcggcgtcggaagacggagacgctcaggcgaatctaatccatgaccat
gagtaa
Figure 10B
MDISNEAGVDAFSIIGPTTIIGRTIAVRILFCNSVSIFRHKVFRILKFFLRGGRVLLSPF
VSLLHPRNPQGILVMVTTMAFLLNRYTSLKAKAEMAYRRKFWRNMMRAALTYEEWSHAAK
MLDKETPKVNETDLFDVELVSNKLDELKHRRHEGSLRDIIFCMRADLVRNLGNMCNPELH
KGRLHVPRLIKEYIDEVSTQLRMVCDMDTEELSLEEKLSFMHETRHAYGRTALLLSGGAS
LGAFHLGVVKTLVEHKLLPRIIAGSSVGSVMCAVVGTRSWPELQSFFEGSWHALQFFDQM
GGIFTTVKRVMTQGAVHEIRHLQWKLRNLTNNLTFQEAYDITGRILGITVCSLRKHEPPR
CLNYLTSPHVVIWSAVTASCAFPGLFEAQELMAKDRTGEIVPYHPPFNLDPEEGSASVRR
WRDGSLEMDLPMIQLKELFNVNHFIVSQANPHIAPFLRMKEFVRACGGRFAAKLAQLAEM
EVKHRCNQVLELGLPLREVASLFAQEWEGDVTIVMPATFSQYLKIIQNPSNVEIQKAANQ
GRRCTWEKLAVIKANFGIELALDECVTVLNHMRRLKRSAERAAAFSAISSSPPSKHLLAG
TNRFNASKRIPSWNCIARQNSSGSVDDDVLAEASRLYQHIVVGSGRNSNRTSNLSHTYDA
GSECDSPEAEDWTRSGGPLMRTNSAQMFTDYVQNLDAVDPEQIRASENDSIVAASSSSHS
ITVTEGDYLQTGRTHNGFVLNLVRGENLRMNSEPEDSQNESEIPETPESVQLDSPEKDII
DGESSASEDGDAQANLIHDHE

Figure 11A

```
atggcgatgtctctccgttccactccattcatctctctccgtacgagaaaaagctttaac
ctttctccgagaattctcgcccttaggttatcatgctgctctggtgggtcttctcaaaat
cagaacttttctacagattccgagaacaagagatcattcgctgttgccaccggtgagctt
ttcatcggaatcgcgtcgaggcttttgaagagttctaatcaaaagacgccgccgattgat
gatggtgatagaatagctagtgtaattgaggatgagattgagccagcgatgatatgggaa
caaagggttaaagatgttgaagcggagaaagagaggagagtcattacaagtcctgggttt
agtttctctgctgctggtcttttgtttccttatcatcttggagttgctcagttgcttatt
gaaaagggttacataaaggaaactactcctttagcaggatcttctgctggtgctatagtc
tgtgctgtgataacctcaggagctactatgcgagaagcccttgaagctactaaggaactt
gcttatgattgtcgacgcaatggcactgctttccgtcttggggctgtccttagagaatcc
atggagaggttactgcccgatgatattcacattaggtccaacgggagaattcgtgttgcc
atcactcaagtgttttggagacctagaggtcttctagtggatcagttcgactccaaaagc
gacttgatagatgcagttttcacatcttcttttattccaggatatcttgcaccaaggcct
gcaacaatgttccgtaatcgactttgtgttgatggaggcttgacattgtttatgccacca
acagctgctgctaaaacagttcgagtttgtgcttttccgctagtaacttcaaactaaag
ggtattgagatctgcccagattgcaaccctttaaacagagcaacatctagacaactattg
aattgggcacttgagccagcagaggacgaggtgttggagaggctgtttgagttaggatac
gcagatgcagctacatgggctgagatgaatccagttgagggattggtctatgacgatact
cctacagctcaagagattcctactagctaa
```

Figure 11B

```
MAMSLRSTPFISLRTRKSFNLSPRILALRLSCCSGGSSQNQNFSTDSENKRSFAVATGEL
FIGIASRLLKSSNQKTPPIDDGDRIASVIEDEIEPAMIWEQRVKDVEAEKERRVITSPGF
SFSAAGLLFPYHLGVAQLLIEKGYIKETTPLAGSSAGAIVCAVITSGATMREALEATKEL
AYDCRRNGTAFRLGAVLRESMERLLPDDIHIRSNGRIRVAITQVFWRPRGLLVDQFDSKS
DLIDAVFTSSFIPGYLAPRPATMFRNRLCVDGGLTLFMPPTAAAKTVRVCAFSASNFKLK
GIEICPDCNPLNRATSRQLLNWALEPAEDEVLERLFELGYADAATWAEMNPVEGLVYDDT
PTAQEIPTS
```

REDUCED RDM-1 GENE EXPRESSION IN PLANTS

This application is a 35 U.S.C. §371 National filing of International Application No. PCT/GB2006/002117, filed Jun. 9, 2006, incorporated herein by reference, which claims priority benefit of Great Britain patent application Nos. 0511810.4, filed Jun. 10, 2005, and 0515510.6, filed Jul. 28, 2005.

The invention relates to nucleic acid molecules encoding plant lipase polypeptides; polypeptides and fragments thereof having lipase activity; transgenic cells expressing said lipase and bioreactors which utilise said lipase nucleic acid molecules and polypeptides.

Phospholipases hydrolyze the ester bonds of phospholipids and are found throughout the plant and animal kingdom. Phospholipids affect metabolism and the construction and organisation of cell membranes and are also involved in regulation of gene expression by modulation of signal transduction pathways that originate at the cell membrane. There are different types of phospholipase which vary in their specificity. Phospholipase A1 hydrolyzes the 1-position fatty acid to produce free fatty acid and 1-lyso-2-acylphospholipid. Phosholipase A2 removes the 2-position fatty acid to produce free fatty acid and 1-acyl-2-lysophospholipid. Phospholipase C removes the phosphate moiety to produce 1,2 diacylglycerol and phosphate base, whilst phospholipase D produces 1,2 diacylglycerophosphate and a base group. A group lipases that are characterised by a conserved amino acid domain are called the patatins are typically phospholipases.

The primary seed storage reserve of many higher plants is triacylglycerol (TAG), which is found in membrane-bound oil bodies. During germination TAG reserves are broken down and the carbon skeletons used to support post-germinative growth. The initial step in the process is catalysed by TAG lipase, which hydrolyses TAG at the oil/water interface to yield free fatty acids and glycerol. In most seeds TAG lipase activity is only detectable upon germination and increases concomitantly with the disappearance of TAG. The free fatty acids released by TAG lipase are subsequently converted to sucrose via the sequential action of β-oxidation, the glyoxylate cycle and gluconeogenesis.

A patatin-like glycoprotein has been partially characterised from potato tubers which has lipid acyl hydrolase activity (see Mignery et al Gene 1988; 62:27-44 and Banflavi et al Mol Gen Genet 1994; 245:517-522) and catalyses the cleavage of fatty acids from membrane lipids. The potato patatin has been implicated as an allergen resulting in various allergic reactions in adults and children for example sneezing, wheezing and contact urticaria.

No plant patatin-like enzyme has been identified that has triacylglycerol lipase activity.

In our co-pending application WO2004/113543, which is incorporated by reference in its entirety, we disclose plant lipase polypeptides which are neutral or acid lipases that have activity toward triacylglycerol. These enzymes are associated with oil bodies via a conserved membrane localisation domain. The present invention is directed to a further lipase which contains a patatin domain, is not homologous to the lipases disclosed in WO2004/113543 and, unlike the partially characterised potato patatin, and has activity toward triacylglycerol. The gene is called Reserve Deposition/Mobilisation 1 (RDM-1) and mutant lines in RDM-1 do not hydrolyze triacylglycerol indicating and essential role for this gene in lipid metabolism.

According to an aspect of the invention there is provided an isolated nucleic acid molecule, or part thereof, which encodes a polypeptide wherein said nucleic acid molecule is selected from the group consisting of:

i) a nucleic acid molecule comprising a nucleic acid sequence as represented in FIG. 1*a*, 9*a* or 10*a*;

ii) a nucleic acid molecule which hybridises to the nucleic acid molecule(s) in (i) and which encodes a polypeptide that has phospholipase and/or triacylglycerol lipase activity.

iii) a nucleic acid molecule that encodes a polypeptide comprising an amino acid sequence as represented in FIG. 1*b*, 9*b* or 10*b*, or a variant polypeptide which is modified by addition, deletion or substitution of at least one amino acid residue wherein said polypeptide has phospholipase and/or triacylglycerol lipase activity.

In a preferred embodiment of the invention said nucleic acid molecule hybridises under stringent hybridisation conditions to a nucleic acid molecule as represented in FIG. 1*a*, 9*a* or 10*a*. Preferably said nucleic acid molecule consists of the nucleic acid sequence represented in FIG. 1*a*, 9*a* or 10*a*.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
    Hybridization: 5×SSC at 65° C. for 16 hours
    Wash twice: 2×SSC at room temperature (RT) for 15 minutes each
    Wash twice: 0.5×SSC at 65° C. for 20 minutes each
High Stringency (Allows Sequences that Share at Least 80% Identity to Hybridize)
    Hybridization: 5×-6×SSC at 65° C.-70° C. for 16-20 hours
    Wash twice: 2×SSC at RT for 5-20 minutes each
    Wash twice: 1×SSC at 55° C.-70° C. for 30 minutes each
Low Stringency (Allows Sequences that Share at Least 50% Identity to Hybridize)
    Hybridization: 6×SSC at RT to 55° C. for 16-20 hours
    Wash at least twice: 2×-3×SSC at RT to 55° C. for 20-30 minutes each.

In a preferred embodiment of the invention said nucleic acid molecule comprises a nucleic acid sequence that has at least or greater than 12% homology to the nucleic acid sequence represented in FIG. 1*a*, 9*a* or 10*a*, or a nucleic acid sequence which encodes an amino acid sequence as represented by FIG. 2, 9*b* or 10*b*. Preferably said homology is at least 20%, 25%, 30%, 35%, 40%; 45%, 50%; 55%, 60%; 65%, 70%; 75%, 80%; 85%; 90%; 95% or at least 99% identity with the nucleic acid sequence represented in FIG. 1*a* 9*a* or 10*a* or a nucleic acid sequence which encodes an amino acid sequence as represented in FIG. 2, 9*b* or 10*b*.

According to an aspect of the invention there is provided a polypeptide encoded by the nucleic acid according to the invention.

According to a further aspect of the invention there is provided an isolated polypeptide which polypeptide comprises an amino acid sequence as shown in FIG. 1b, 9b or 10b or FIG. 2, or a variant polypeptide which is modified by addition, deletion or substitution of at least one amino acid residue wherein said polypeptide has phospholipase and/or triacylglycerol lipase activity.

A variant polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants which retain or enhance the same biological function and activity as the reference polypeptide from which it varies.

In addition, the invention features polypeptide sequences having at least or greater than 12% identity with the polypeptide sequences as herein disclosed, or fragments and functionally equivalent polypeptides thereof.

In one embodiment, the polypeptides have at least 20% identity, more preferably at least 25%, 30%, 35%, 40%, 45%, 50%, 55%, 60%, 65%, 70%, 75%, 80%, 85%, 90%, 95%, or 99% identity with the amino acid sequences illustrated herein.

According to a further aspect of the invention there is provided a vector comprising a nucleic acid molecule according to the invention. Preferably said vector is an expression vector adapted for the expression of a polypeptide according to the invention.

Preferably the nucleic acid in the vector is operably linked to an appropriate promoter or other regulatory elements for transcription in a host cell such as a prokaryotic, (e.g. bacterial), or eukaryotic (e.g. fungal, plant, mammalian or insect cell). The vector may be a bi-functional expression vector which functions in multiple hosts. In the example of nucleic acids encoding polypeptides according to the invention this may contain its native promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al (1985) Nature 313, 9810-812); rice actin (McElroy et al (1990) Plant Cell 2: 163-171); ubiquitin (Christian et al. (1989) Plant Mol. Biol. 18 (675-689); pEMU (Last et al (1991) Theor Appl. Genet. 81: 581-588); MAS (Velten et al (1984) EMBO J. 3. 2723-2730); ALS promoter (U.S. application Ser. No. 08/409,297), and the like. Other constitutive promoters include those in U.S. Pat. Nos. 5,608,149; 5,608,144; 5,604,121; 5,569,597; 5,466,785; 5,399,680, 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al (1991) Proc. Natl. Acad. Sci. USA 88: 10421-10425 and McNellie et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al (1997) Plant Cell Physiol. 38(7): 792-803; Hansen et al (1997) Mol. Gen. Genet. 254(3): 337-343; Russell et al. (1997) Transgenic Res. 6(2): 157-168; Rinehart et al (1996) Plant Physiol. 112(3): 1331-1341; Van Camp et al (1996) Plant Physiol. 112(2): 525-535; Canevascni et al (1996) Plant Physiol. 112(2): 513-524; Yamamoto et al (1994) Plant Cell Physiol. 35(5): 773-778; Lam (1994) Results Probl. Cell Differ. 20: 181-196; Orozco et al (1993) Plant Mol. Biol. 23(6): 1129-1138; Mutsuoka et al (1993) Proc. Natl. Acad. Sci. USA 90(20): 9586-9590; and Guevara-Garcia et al (1993) Plant J. 4(3): 495-50.

In a preferred embodiment of the invention said tissue specific promoter is a promoter which is active during the accumulation of oil in developing oil seeds, (for example see Broun et al. (1998) Plant J. 13(2): 201-210.

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is an inducible promoter or a developmentally regulated promoter.

Particular vectors are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP-A-194809).

Vectors may also include selectable genetic marker such as those that confer selectable phenotypes such as resistance to herbicides (e.g. kanamycin, hygromycin, phosphinothricin, chlorsulfuron, methotrexate, gentamycin, spectinomycin, imidazolinones and glyphosate).

Alternatively, or in addition, said vectors are vectors suitable for mammalian cell transfection or yeast cell transfection. In the latter example multi-copy vectors such as 2µ episomal vectors are preferred. Alternatively yeast CEN vectors and integrating vectors such as YIP vectors are suitable for transformation of yeast species such as *Saccharomyces cerevisiae* and *Pichia* spp.

According to a further aspect of the invention there is provided a cell transfected or transformed with at least one nucleic acid molecule or vector according to the invention.

In a preferred embodiment of the invention said cell is eukaryotic cell.

Preferably said eukaryotic cell is selected from the group consisting of: mammalian cells (e.g. Chinese Hamster Ovary cells); yeast cells (e.g. *Saccharomyces* spp, *Pichia* spp); algal cells (e.g *Phaeodactylum tricornutum, Chlamydomonas reinhardtii*); insect cells (e.g. *Spodoptera* spp) or plant cells.

In a preferred embodiment of the invention said cell is a plant cell.

In a preferred embodiment of the invention said plant is selected from: corn (*Zea mays*), canola (*Brassica napus, Brassica rapa* ssp.), flax (*Linum usitatissimum*), alfalfa (*Medicago sativa*), rice (*Oiyza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plants of the present invention are crop plants (for example, cereals and pulses, maize, wheat, potatoes, tapioca, rice, sorghum, millet, cassava, barley, pea), and other root, tuber or seed crops. Important seed crops are oil-seed rape, sugar beet, maize, sunflower, soybean, sorghum, and flax (linseed). Horticultural plants to which the present invention may be applied may include lettuce, endive, and vegetable brassicas including cabbage, broccoli, and cauliflower. The present invention may be applied in tobacco, cucurbits, carrot, strawberry, sunflower, tomato, pepper.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

In a further preferred embodiment of the invention said cell is a prokaryotic cell.

In a preferred embodiment of the invention said cell is transfected or transformed with at least one further nucleic acid molecule wherein said nucleic acid molecule is selected from the following group:
  i) a nucleic acid molecule comprising a nucleic acid sequence as represented in FIG. 3a or 4a;
  ii) a nucleic acid molecule which hybridises to the nucleic acid molecule in (i) under stringent hybridisation conditions and which encodes a polypeptide that has triacylglycerol lipase activity;
  iii) a nucleic acid molecule which differs from the nucleic acid molecules of (i) and (ii) due to the degeneracy in the genetic code.

Preferably said nucleic acid molecule consists of the nucleic acid sequence represented in FIG. 3a or 4a.

In a further preferred embodiment of the invention said lipase is an acid lipase.

In an alternative preferred embodiment of the invention said lipase is a neutral lipase.

According to a further aspect of the invention there is provided a seed comprising a plant cell according to the invention. Preferably said seed is from an oil seed plant.

In a preferred embodiment of the invention said cell overexpresses the nucleic acid molecule(s) according to the invention when compared to a non-transgenic reference cell of the same species. Preferably said cell has increased phospholipase and/or triacylglycerol lipase activity.

In a further preferred embodiment of the invention said cell over-expresses said nucleic acid molecule(s) by at least 2-fold above basal level expression. Preferably said cell over-expresses by at least 5-fold; 10-fold, 20-fold, 30-fold, 40-fold, or 50-fold. Preferably said cell expresses said nucleic acid by at least 100-fold above basal level expression when compared to a non-transgenic cell of the same species.

It will be apparent that means to increase the activity of a polypeptide encoded by a nucleic acid molecule are known to the skilled artisan. For example, and not by limitation, increasing the gene dosage by providing a cell with multiple copies of said gene. Alternatively or in addition, a gene(s) may be placed under the control of a powerful promoter sequence or an inducible promoter sequence to elevate expression of mRNA encoded by said gene. The modulation of mRNA stability is also a mechanism used to alter the steady state levels of an mRNA molecule, typically via alteration to the 5' or 3' untranslated regions of the mRNA.

In an alternative preferred embodiment of the invention there is provided a plant cell which is modified such that the expression of the nucleic acid molecule according to the invention is decreased when compared to a non-modified plant cell of the same species.

In a preferred embodiment of the invention said cell is modified to reduce the expression of said nucleic acid molecule wherein phospholipase and/or triacylglycerol lipase activity is reduced by at least 10% when compared to a non-modified reference cell of the same species. Preferably said activity is reduced by between about 10%-90%. More preferably said activity is reduced by at least 20%, 30%, 40%, 50%, 60%, 70%, 80% or at least 90%.

In a preferred embodiment of the invention said plant cell is null for a nucleic acid molecule comprising a sequence selected from the group consisting of:
  i) the nucleic acid molecule comprising a sequence as represented by FIG. 1a, 9a, 10a, 3 or 4;
  ii) nucleic acids which hybridise to the sequences of (i) above and which encode a polypeptide that has phospholipase and/or triacylglycerol lipase activity; and
  iii) nucleic acid sequences which are degenerate as a result of the genetic code to the sequences defined in (i) and (ii) above.

Null refers to a cell that includes a non-functional copy of the nucleic acid sequence described above wherein the activity of the polypeptide encoded by said nucleic acid is ablated. Methods to provide such a cell are well known in the art and include the use of antisense genes to regulate the expression of specific targets; insertional mutagenesis using T-DNA; the introduction of point mutations and small deletions into open reading frames and regulatory sequences; and double stranded inhibitory RNA (RNAi).

A number of techniques have been developed in recent years that purport to specifically ablate genes and/or gene products. A recent technique to specifically ablate gene function is through the introduction of double stranded RNA, also referred to as inhibitory RNA (RNAi), into a cell that results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from exonic or coding sequence of the gene which is to be ablated. Surprisingly, only a few molecules of RNAi are required to block gene expression that implies the mechanism is catalytic. The site of action appears to be nuclear as little if any RNAi is detectable in the cytoplasm of cells indicating that RNAi exerts its effect during mRNA synthesis or processing.

An alternative embodiment of RNAi involves the synthesis of so called "stem loop RNAi" molecules that are synthesised from expression cassettes carried in vectors. The DNA molecule encoding the stem-loop RNA is constructed in two parts, a first part that is derived from a gene the regulation of which is desired. The second part is provided with a DNA sequence that is complementary to the sequence of the first part. The cassette is typically under the control of a promoter that transcribes the DNA into RNA. The complementary nature of the first and second parts of the RNA molecule results in base pairing over at least part of the length of the RNA molecule to form a double stranded hairpin RNA structure or stem-loop. The first and second parts can be provided with a linker sequence. Stem loop RNAi has been successfully used in plants to ablate specific mRNA's and thereby affect the phenotype of the plant, see, Smith et al (2000) Nature 407, 319-320.

In a preferred embodiment of the invention there is provided a plant cell wherein said cell is transfected with a nucleic acid molecule comprising an expression cassette which cassette comprises a nucleic acid sequence which encodes at least part of a phospholipase and/or triacylglycerol lipase as herein described wherein said cassette is adapted such that both sense and antisense nucleic acid molecules are transcribed from said cassette.

In a preferred embodiment of the invention said cassette is provided with at least two promoters adapted to transcribe sense and antisense strands of said nucleic acid molecule.

In a further preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts.

According to a further aspect of the invention there is provided a nucleic acid molecule comprising an expression cassette which cassette comprises a nucleic acid sequence which encodes at least part of a phospholipase and/or triacylglycerol lipase as herein described wherein said cassette is adapted such that both sense and antisense nucleic acid molecules are transcribed from said cassette.

In a preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts.

In a preferred embodiment of the invention said first and second parts are linked by at least one nucleotide base. In a further preferred embodiment of the invention said first and second parts are linked by 2, 3, 4, 5, 6, 7, 8, 9, or 10 nucleotide bases. In a yet further preferred embodiment of the invention said linker is at least 10 nucleotide bases.

In a further preferred embodiment of the invention the length of the RNA molecule is between 10 nucleotide bases (nb) and 1000 nb. Preferably said RNA molecule is at least 100 nb; 200 nb; 300 nb; 400 nb; 500 nb; 600 nb; 700 nb; 800 nb; 900 nb; or 1000 nb in length. More preferably still said RNA molecule is at least 1000 nb in length. Preferably still said RNA molecule is 21 nb in length.

According to a further aspect of the invention there is provided a method to manufacture a polypeptide according to the invention comprising the steps of:

i) providing a cell according to the invention and growth conditions conducive to the production of a polypeptide according to the invention; and optionally ii) purifying said polypeptide from said cell or growth media.

According to a yet further aspect of the invention there is provided the use of a polypeptide encoded by a nucleic acid according to the invention as a target for the discovery of agents that inhibit the lipase activity of said polypeptide.

According to a further aspect of the invention there is provided a screening method for the identification of an agent with the ability to inhibit plant growth and/or viability comprising the steps of:

i) providing a polypeptide encoded by a nucleic acid molecule selected from the following group;

a) a nucleic acid molecule comprising a nucleic acid sequence as represented in FIG. 1*a*, 9*a* or 10*a*;

b) a nucleic acid molecule that hybridises to the nucleic acid molecule(s) in (i) and which encodes a polypeptide that has phospholipase and/or triacylglycerol lipase activity;

c) a nucleic acid molecule that encodes a polypeptide comprising an amino acid sequence as represented in FIG. 1*b*, or a variant polypeptide which is modified by addition, deletion or substitution of at least one amino acid residue wherein said polypeptide has phospholipase and/or triacylglycerol lipase activity;

ii) providing at least one candidate agent;

iii) forming a preparation which is a combination of (i) and (ii);

iv) determining the interaction of the polypeptide and said candidate agent; and testing the effect of the agent on the growth and/or viability of plants.

In a preferred method of the invention said agent is a herbicide.

According to a yet further aspect of the invention there is provided a reaction vessel comprising the polypeptide according to the invention, fatty acid substrates and co-factors. In particular, protein molecules which comprise the sequences as represented by FIGS. 1*a*, 9*a* or 10*a* and/or FIG. 2 and/or FIG. 3, or sequence variants thereof which are herein disclosed.

In a preferred embodiment of the invention said at least one polypeptide is expressed by a cell according to the invention.

In a preferred embodiment of the invention said polypeptide(s) is/are soluble. Alternatively said polypeptide(s) is/are immobilised.

In a further preferred embodiment of the invention said vessel is a bioreactor.

It will be apparent to one skilled in the art that a polypeptide according to the invention has utility with respect to the in vivo catabolism of fatty acids through transformation or transfection of nucleic acids encoding said polypeptide(s) into suitable host cells. Cells expressing said polypeptide (s) can also be incubated under suitable growth conditions to facilitate the conversion of fatty acids. Alternatively, said polypeptide (s) can either be purified from a cell culture or manufactured recombinantly and used in a bioreactor to convert fatty acids in vitro.

According to a further aspect of the invention there is provided a method to increase the fatty acid content of a seed comprising the steps of:
  i) cultivating a plant according to claim 16 or 17 to produce seed;
  ii) harvesting said seed from said plant; and optionally
  iii) determining the fatty acid content of said harvested seed.

According to a further aspect of the invention there is provided an isolated cell wherein said cell is a transgenic cell and is transformed with a vector comprising a nucleic acid molecule wherein said nucleic acid molecule is selected from the group consisting of:
  i) a nucleic acid molecule comprising a nucleic acid sequence as represented in FIG. 11a;
  ii) a nucleic acid molecule which hybridises under stringent hybridisation conditions to the nucleic acid molecule(s) in (i) and which has phospholipase and/or triacylglycerol lipase activity;
  iii) a nucleic acid molecule that encodes a polypeptide comprising an amino acid sequence as represented in FIG. 11b, or a variant polypeptide which is modified by addition, deletion or substitution of at least one amino acid residue wherein said polypeptide has phospholipase and/or triacylglycerol lipase activity.

According to a further aspect of the invention said cell is transformed with a nucleic acid molecule comprising an expression cassette which cassette comprises a nucleic acid sequence selected from the group consisting of:
  i) a nucleic acid molecule comprising a nucleic acid sequence as represented in FIG. 11a;
  ii) a nucleic acid molecule which hybridises under stringent hybridisation conditions to the nucleic acid molecule(s) in (i) and which encodes a polypeptide that has phospholipase and/or triacylglycerol lipase activity;
  iii) a nucleic acid molecule that encodes a polypeptide comprising an amino acid sequence as represented in FIG. 11b, or a variant polypeptide which is modified by addition, deletion or substitution of at least one amino acid residue wherein said polypeptide has phospholipase and/or triacylglycerol lipase activity; wherein said cassette is adapted such that both sense and antisense nucleic acid molecules are transcribed from said cassette.

According to a further aspect of the invention there is provided a plant or seed comprising a plant cell according to the invention.

According to a further aspect of the invention there is provided the use of a polypeptide encoded by a nucleic acid molecule selected from the group consisting of:
  i) a nucleic acid molecule comprising a nucleic acid sequence as represented in FIG. 11a;
  ii) a nucleic acid molecule which hybridises under stringent hybridisation conditions to the nucleic acid molecule(s) in (i) and which encodes a polypeptide that has phospholipase and/or triacylglycerol lipase activity;
  iii) a nucleic acid molecule that encodes a polypeptide comprising an amino acid sequence as represented in FIG. 11b, or a variant polypeptide which is modified by addition, deletion or substitution of at least one amino acid residue wherein said polypeptide has phospholipase and/or triacylglycerol lipase activity, as a target for the discovery of agents that inhibit the lipase activity of said polypeptide.

According to a further aspect of the invention there is provided a screening method for the identification of an agent with the ability to inhibit plant growth and/or viability comprising the steps of:
  i) providing a polypeptide encoded by the nucleic acid selected from the following group;
    a) a nucleic acid molecule comprising a nucleic acid sequence as represented in FIG. 11a;
    b) a nucleic acid molecule which hybridises to the nucleic acid molecule(s) in (i) and which encodes a polypeptide that has phospholipase and/or triacylglycerol lipase activity;
    c) a nucleic acid molecule that encodes a polypeptide comprising an amino acid sequence as represented in FIG. 11b, or a variant polypeptide which is modified by addition, deletion or substitution of at least one amino acid residue wherein said polypeptide has phospholipase and/or triacylglycerol lipase activity;
  ii) providing at least one candidate agent;
  iii) forming a preparation which is a combination of (i) and (ii);
  iv) determining the interaction of the polypeptide and said candidate agent; and testing the effect of the agent on the growth and/or viability of plants.

According to a further aspect of the invention there is provided a reaction vessel comprising the polypeptide encoded by a nucleic acid molecule selected from the group consisting of:
  i) a nucleic acid molecule comprising a nucleic acid sequence as represented in FIG. 11a;
  ii) a nucleic acid molecule which hybridises under stringent hybridisation conditions to the nucleic acid molecule(s) in (i) and which encodes a polypeptide that has phospholipase and/or triacylglycerol lipase activity;
  iii) a nucleic acid molecule that encodes a polypeptide comprising an amino acid sequence as represented in FIG. 11b, or a variant polypeptide which is modified by addition, deletion or substitution of at least one amino acid residue wherein said polypeptide has phospholipase and/or triacylglycerol lipase activity, fatty acid substrates and co-factors.

According to a further aspect of the invention there is provided a method to increase the fatty acid content of a seed comprising the steps of:
  i) cultivating a plant according to the invention to produce seed;
  ii) harvesting said seed from said plant; and optionally
  iii) determining the fatty acid content of said harvested seed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following figures:

FIG. 1a (SEQ ID NO: 1) is the complete nucleotide sequence of reserve deposition mobilisation 1 (RDM1); FIG. 1b (SEQ ID NO: 2) is the amino acid sequence of the conserved patatin domain of RDM1;

FIG. 2 (SEQ ID NO: 3) is the amino acid sequence of RDM-1;

FIG. 3a (SEQ ID NO: 4) is the nucleotide sequence of OBL1; FIG. 3b (SEQ ID NO: 5) is the amino acid sequence of OBL1;

FIG. 4a (SEQ ID NO: 6) is the nucleotide sequence of OBL2; FIG. 4b (SEQ ID NO: 7) is the amino acid sequence of OBL2;

FIG. 5 is a sequence comparison of potato (SEQ ID NO: 20) and *Arabidopsis thaliana* (amino acids 243-390 of SEQ ID NO: 2) patatin-like conserved domains;

Figure 8:
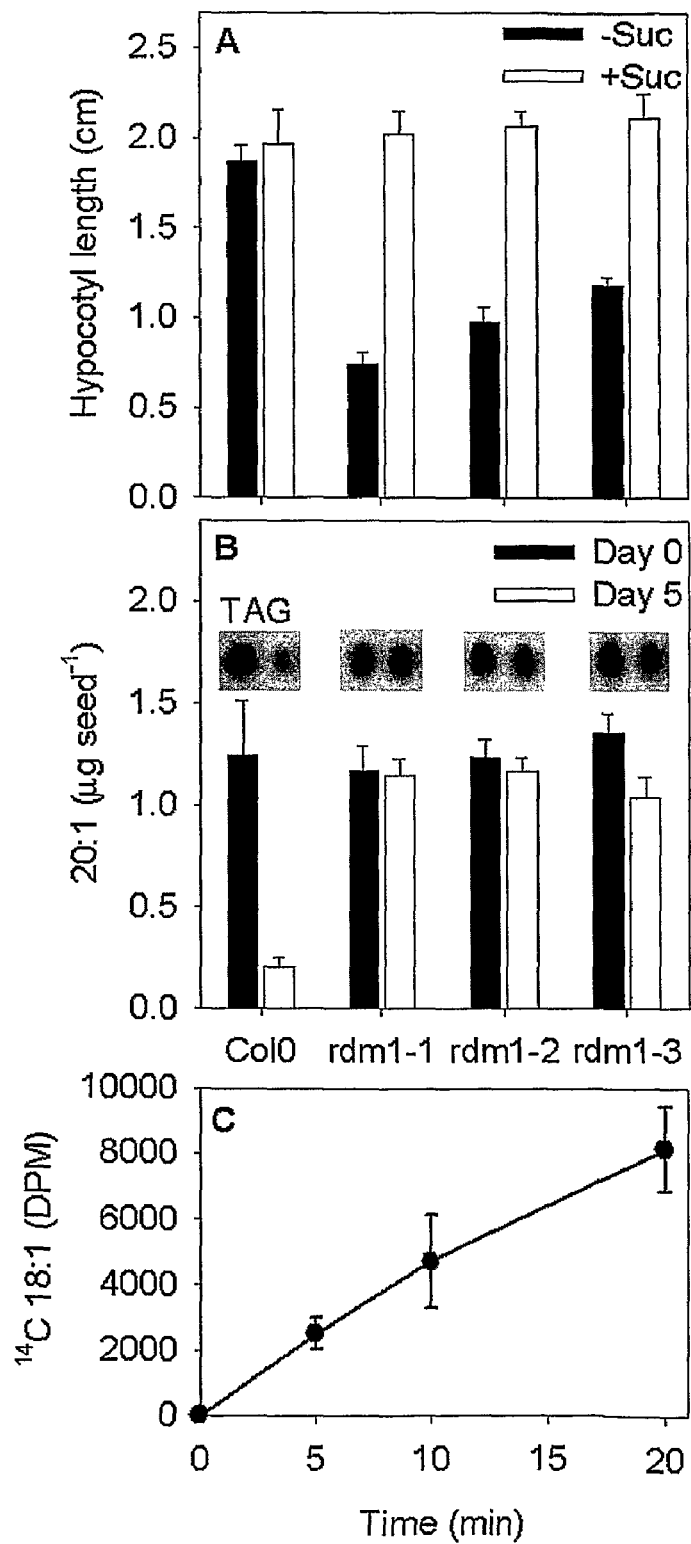

FIGS. 6A and 6B illustrate the mutations rdm1-1 (SEQ ID NOs: 8 and 11), rdm1-2 (SEQ ID NOs: 9 and 12) and rdm1-3 (SEQ ID NOs: 10 and 13) induced by EMS mutagenesis in the RDM1 wild-type sequence;

FIG. 7 illustrates the homology between RDM1 (amino acids 110-567 of SEQ ID NO: 2) and the yeast gene TGL3 (YMR313c) (SEQ ID NO: 21); and FIG. 8 illustrates the effects of mutations rdm1-1, rdm1-2 and rdm1-3 on hypocotyls length (A), 11-eicosenoic acid (20:1 n9) and triacylglycerol content of seeds (B) and release of 20:1 fatty acid from triacylglycerol by RDM1 (C);

FIG. 9A (SEQ ID NO: 14) is a *Ricinus communis* RDM1-like partial cDNA sequence; FIG. 9B (SEQ ID NO: 15) is a translation of the partial *Ricinus communis* cDNA;

FIG. 10A (SEQ ID NO: 16) is an *Arabidopsis* RDM1-like cDNA sequence; FIG. 10B (SEQ ID NO: 17) is a translation of the RDM1-like cDNA sequence;

FIG. 11A (SEQ ID NO: 18) is an *Arabidopsis* patatin-like cDNA sequence; FIG. 11B (SEQ ID NO: 19) is a translation of the patatin-like cDNA sequence; and Table 1 illustrates total fatty acid content and weight of wild type and rdm1 seeds.

MATERIALS AND METHODS

Plant Material and mutant selection—Wild-type *Arabidopsis thaliana* (ecotype Colombia 0 and Landsberg erecta) were obtained from the Nottingham *Arabidopsis* Stock Centre (University of Nottingham, UK). M2 EMS mutagenized Col0 seed was obtained from Lehle Seeds (Round Rock, Tex., USA). For the screen mutant seed >250 µM in diameter was selected using a sieve. Approximately 240,000 seed was sterilised, applied to agar plates containing ½ strength MS salts (pH 5.7) (Murashige, T. and Skoog, F. (1962) *Physiol Plant.* 15, 473-496) and imbibed at 4° C. for four days. The plates were then exposed to white light (PPFD=150 µmol m$^{-2}$ s$^{-1}$) for 30 min and transferred to the dark for five days at 21° C. Seedlings that had short hypocotyls were selected and rescued onto agar plates containing ½ strength MS salts plus 30 mM sucrose (pH 5.7). The seedlings were grown on plates until they were photosynthetically competent and then transferred to soil and grown to seed in the glasshouse.

Mapping—The rdm1-1 mutant was out-crossed to wild type ecotype Landsberg erecta. F1 plants were allowed to self fertilise and the F2 progeny were screened for sugar dependence. Genomic DNA was isolated from ~1000 F2 rdm1-1 lines. Mapping was carried out using simple sequence polymorphisms (Bell, C. J. and Ecker, J. R. (1994) *Genomics* 19, 137-144) and cleaved amplified polymorphic sequences (Konieczny, A and Ausubel, F. M. (1993) *Plant J.* 4, 403-410). rdm1 was located on Chromosome 5 to a region between genes At5g04030 and At5g04060. Sequencing genomic DNA from three independent rdm1 alleles revealed that all three have mutations in At5g04040.

Lipid analysis—Fatty acids were extracted from seeds and seedlings, converted to methyl esters and quantified by gass chromatography according to the method of Browse, J., McCourt, P. J. and Somerville, C. R. (1986) *Anal. Biochem.* 152, 141-145. Total lipids were extracted according tho the method of Folch, J., Lees, M. and Sloane Stanley, G. H. (1957) *J. Biol. Chem.* 226, 449-509. The neutral lipids were then separated by Thin Layer Chromatography according to Lehner, R. and Verger, R. (1997) *Biochemistry* 36, 1861-1868 before being sprayed with 50% (v/v) HCl and visualized by charing at 180° C.

Expression of RDM1 and lipase assays—The RDM1 cDNA sequence was amplified by RT-PCR from RNA extracted from seeds. It was cloned into the pYES2.1/V5-His-TOPO vector (from Invitrogen). The vector was transformed into *S. cerevisiae* INVSc1 cells the protein expressed following the pYES2.1 TOPO Expression Kit instructions. The 6×His tagged protein was extracted and purified as described by Athenstaedt, K and Daum, G. (2003) J. Biol. Chem. 278, 23317-23323.

Assays were performed on the purified protein using emulsified radiolabelled [$^{14}$C]triolein as a substrate. Reactions were carried out at 30° C. in a 100 µl reaction mixture consisting of 100 mM potassium phosphate buffer (pH 8) plus 100 mM NaCl$_2$, 1 µg ml$^{-1}$ bovine serum albumin and substrate. The substrate was emulsified in 5% (w/v) gum arabic using sonication and 10 µl added to the assay mixture. Reactions were stopped by the addition of 1 ml of chloroform: methanol heptane (1.25:1.41:1 v/v/v) and 72 µl of 0.2 M NaOH, 150 mM NaCl$_2$ plus lipid carrier (50 µg of oleic acid, mono-, di- and trioleoylglycerol). The reactions were vortexed and centrifuged for 5 min at 10,000 g. 0.4 ml of the upper phase was removed and subjected to liquid scintillation counting.

Total fatty acid content and weight of wild type and rdm1 seeds.

Experiment 1.

| Seed | Total fatty acid content (µg seed$^{-1}$) | Seed weight (µg seed$^{-1}$) | % oil content |
| --- | --- | --- | --- |
| Col0 | 8.13 ± 0.11 | 21.8 ± 0.08 | 37.3 |
| rdm1-1 | 8.99 ± 0.25 | 21.7 ± 0.05 | 41.4 |
| rdm1-2 | 8.82 ± 0.23 | 22.1 ± 0.08 | 39.9 |
| rdm1-3 | 8.62 ± 0.19 | 21.9 ± 0.09 | 39.4 |

Experiment 2.

| Seed | Total fatty acid content (µg seed$^{-1}$) | Seed weight (µg seed$^{-1}$) | % oil content |
| --- | --- | --- | --- |
| Col0 | 8.51 ± 0.21 | 23.7 ± 0.06 | 35.9 |
| rdm1-1 | 9.31 ± 0.26 | 23.4 ± 0.07 | 39.8 |
| rdm1-2 | 9.27 ± 0.17 | 22.9 ± 0.14 | 40.5 |
| rdm1-3 | 9.10 ± 0.19 | 23.9 ± 0.04 | 38.1 |

*Arabidopsis* plants were grown to seed in the glasshouse in P15 trays containing F2 compost. The total fatty acid content of batches of 50 seeds was measured by gas chromatography following direct extraction/methylation (Browse et al., (1986) Anal. Biochem. 152, 141). Seed weights were measured for batches of 500 seeds. Values are the mean ±standard error of measurements from 15 separate plants.

The invention claimed is:

1. A plant cell wherein said cell is transformed with a nucleic acid molecule comprising an expression cassette which cassette comprises a nucleic acid molecule selected from the group consisting of:
   i) a nucleic acid molecule comprising a nucleic acid sequence as represented in SEQ ID NO: 1;
   ii) a nucleic acid molecule which hybridises under stringent hybridisation conditions comprising hybridization at a temperature of 65-70° C. for 16 hours in 5-6X SSC to the complement of the nucleic acid molecule in (i) and which comprises a nucleotide sequence that encodes a polypeptide that has phospholipase and/or triacylglycerol lipase activity; and
   iii) a nucleic acid molecule that comprises a nucleotide sequence that encodes a polypeptide comprising an amino acid sequence as represented in SEQ ID NO: 2, or a variant polypeptide which is modified by addition, deletion or substitution of at least one amino acid residue, said variant polypeptide having an amino acid sequence with at least 90% identity to the amino acid sequence represented in SEQ ID NO:2, wherein said polypeptide or variant polypeptide has phospholipase and/or triacylglycerol lipase activity;
   wherein said cassette is adapted such that both sense and antisense nucleic acid molecules are transcribed from said cassette.

2. A plant cell according to claim 1 wherein said cassette is provided with at least two promoters adapted to transcribe sense and antisense strands of said nucleic acid molecule.

3. A plant cell according to claim 1 wherein said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts.

4. A transgenic plant comprising a cell according to claim 1.

5. A transgenic plant according to claim 4 wherein said plant is an oil seed plant.

6. A method to increase the fatty acid content of a seed comprising the steps of:
   i) cultivating a plant according to claim 4 to produce seed; and
   ii) harvesting said seed from said plant.

7. The method of claim 6, further comprising:
   iii) determining the fatty acid content of said harvested seed.

8. A seed comprising a plant cell according to claim 1.

9. A seed according to claim 8 wherein said seed is from an oil seed plant.

10. The plant cell according to claim 1, wherein the nucleic acid molecule comprises a nucleic acid sequence as represented in SEQ ID NO: 1.

11. A plant cell wherein said cell is transformed with a nucleic acid molecule comprising an expression cassette that comprises a nucleic acid molecule selected from the group consisting of:
   i) a nucleic acid molecule comprising the nucleic acid sequence set forth in SEQ ID NO: 1; and
   ii) a nucleic acid molecule that comprises a nucleotide sequence that encodes a polypeptide comprising the amino acid sequence set forth in SEQ ID NO: 2;
   wherein said cassette is adapted such that both sense and antisense nucleic acid molecules are transcribed from said cassette.

12. A transgenic plant comprising a cell according to claim 11.

13. A transgenic plant according to claim 12, wherein said plant is an oil seed plant.

14. A seed comprising a plant cell according to to claim 11.

15. A seed according to claim 14, wherein said seed is from an oil seed plant.

\* \* \* \* \*

SEQUENCE LISTING

<160> NUMBER OF SEQ ID NOS: 21

<210> SEQ ID NO 1
<211> LENGTH: 2478
<212> TYPE: DNA
<213> ORGANISM: Arabidopsis thaliana

<400> SEQUENCE: 1

| | | | | | |
|---|---|---|---|---|---|
| atggatataa | gtaatgaggc | tagtgtcgat | cccttttcga | ttggaccatc | atctatcatg | 60 |
| ggtcgaacca | ttgctttcag | agtcttgttc | tgtagatcaa | tgtcacagct | taggcgtgat | 120 |
| ctctttcggt | tcttgttgca | ttggtttctt | agatttaagc | tgaccgtttc | accgtttgtg | 180 |
| tcgtggtttc | atcctcggaa | ccctcaaggg | attttagcgg | tggttacaat | cattgccttt | 240 |
| gtgttgaaac | gatacacgaa | tgtgaaaata | aaggcggaaa | tggcttaccg | gaggaagttt | 300 |
| tggaggaata | tgatgcggac | ggctttgact | tatgaggaat | gggctcatgc | tgctaagatg | 360 |
| ttagagaagg | aaacaccaaa | gatgaatgaa | tctgatcttt | atgatgaaga | gttggttaag | 420 |
| aacaagcttc | aggagcttcg | tcatcgtcgc | caagaaggct | cacttagaga | cattatgttt | 480 |
| tgtatgagag | ctgatttggt | gaggaatctc | ggtaatatgt | gtaattcgga | gcttcataaa | 540 |
| ggtagacttc | aggttcctag | acatatcaaa | gagtacattg | atgaggtgtc | tactcagttg | 600 |
| agaatggttt | gtaactctga | ttcagaggag | ctttctttag | aagagaagct | ttcttttatg | 660 |
| catgaaacac | ggcatgcctt | tggtagaacg | gctttgcttt | tgagtggtgg | ggcttctctt | 720 |
| ggtgcgtttc | atgttggtgt | ggttaggact | ttggttgagc | ataagctttt | acctcgaata | 780 |
| attgctggtt | ctagtgttgg | atccatcatt | tgtgctgttg | tggcctcaag | gtcttggcca | 840 |
| gaactacaga | gtttctttga | gaattctttg | cattctttac | agttctttga | tcagctcgga | 900 |
| ggcgtgttct | caatagtgaa | acgggtaatg | acacaagggg | ctctacacga | tatcagacag | 960 |
| ttgcaatgta | tgcttagaaa | cctcacaagc | aatctcacat | tccaagaagc | ttatgacatg | 1020 |
| acaggaagga | ttctcgggat | caccgtttgc | tccccaagaa | agcatgaacc | tcctcggtgt | 1080 |
| cttaactatt | tgacttcgcc | tcatgtggtt | atatggagcg | cagtgactgc | ttcttgtgct | 1140 |
| tttcctggtc | tcttttgaagc | tcaagagcta | atggctaaag | atcgaagtgg | agagatcgta | 1200 |
| ccgtatcatc | cacctttcaa | tttggatcca | gaagtaggca | ctaaatcatc | atctggacgc | 1260 |
| cggtggagag | atggtagttt | ggaggttgat | ttaccaatga | tgcagcttaa | agaactgttc | 1320 |
| aatgtcaatc | attttattgt | gagccaagcc | aatcctcaca | ttgctccatt | actgcgtcta | 1380 |
| aaggatttag | ttcgagctta | tggtggtaga | ttcgcagcta | agctcgcgca | tctagtggag | 1440 |
| atggaggtca | aacatagatg | caaccaggta | ttagagctcg | gttttcctct | cggtggactc | 1500 |
| gcaaagcttt | ttgctcagga | gtgggaaggt | gatgttacag | ttgtaatgcc | tgctactctt | 1560 |
| gctcagtact | cgaagattat | acaaaatccg | actcatgtcg | agcttcagaa | agcggctaac | 1620 |
| caaggaagaa | gatgcacttg | ggagaagctc | tcagccataa | aatcaaactg | cgggatcgag | 1680 |
| cttgcgcttg | atgattctgt | agctattctt | aaccatatgc | ggaggctcaa | gaaaagtgcg | 1740 |
| gagagagccg | ccactgccac | gtcttcgtct | catcacggat | tggcttcaac | caccagattc | 1800 |
| aatgcttcaa | gaagaatccc | atcttggaac | gtccttgcca | gagagaactc | aacaggctca | 1860 |
| ctggatgatc | tagtcactga | caataacctc | cacgcttctt | cgggcaggaa | tttaagcgac | 1920 |
| agtgaaacag | agagcgtgga | gttgagttct | tggacaagaa | ctggtggacc | tttaatgaga | 1980 |

```
acagcttctg ctaataagtt cattgatttt gttcagagtc ttgatatcga cattgcattg    2040
gtcagaggat ttagtagcag tcccaattct ccagcagttc ctcctggtgg ctcgtttact    2100
ccaagcccga gatccatagc ggctcattcg gatatcgaat caaacagcaa tagcaacaat    2160
cttggaacaa gcacttcaag cataacagtt actgaaggtg atcttctaca gcctgagaga    2220
acgagtaacg gatttgtgtt aaacgtcgtt aaaagagaga acttgggaat gccatcgatt    2280
gggaaccaaa atacagagtt accagagagt gtacagctcg atataccgga gaaggagatg    2340
gattgtagct ctgtatcaga acacgaagaa gatgataacg acaatgaaga agaacataac    2400
ggctcgagtc tggttactgt ttcttcagaa gattccggtt tacaagaacc ggtgtctggt    2460
agtgttatag atgcttag                                                  2478
```

<210> SEQ ID NO 2
<211> LENGTH: 142
<212> TYPE: PRT
<213> ORGANISM: Arabidopsis thaliana

<400> SEQUENCE: 2

```
His Val Gly Val Val Arg Thr Leu Val Glu His Lys Leu Leu Pro Arg
1               5                   10                  15

Ile Ile Ala Gly Ser Ser Val Gly Ser Ile Ile Cys Ala Val Val Ala
            20                  25                  30

Ser Arg Ser Trp Pro Glu Leu Gln Ser Phe Phe Glu Asn Ser Leu His
        35                  40                  45

Ser Leu Gln Phe Phe Asp Gln Leu Gly Gly Val Phe Ser Ile Val Lys
    50                  55                  60

Arg Val Met Thr Gln Gly Ala Leu His Asp Ile Arg Gln Leu Gln Cys
65                  70                  75                  80

Met Leu Arg Asn Leu Thr Ser Asn Leu Thr Phe Gln Glu Ala Tyr Asp
                85                  90                  95

Met Thr Gly Arg Ile Leu Gly Ile Thr Val Cys Ser Pro Arg Lys His
            100                 105                 110

Glu Pro Pro Arg Cys Leu Asn Tyr Leu Thr Ser Pro His Val Val Ile
        115                 120                 125

Trp Ser Ala Val Thr Ala Ser Cys Ala Phe Pro Gly Leu Phe
    130                 135                 140
```

<210> SEQ ID NO 3
<211> LENGTH: 825
<212> TYPE: PRT
<213> ORGANISM: Arabidopsis thaliana

<400> SEQUENCE: 3

```
Met Asp Ile Ser Asn Glu Ala Ser Val Asp Pro Phe Ser Ile Gly Pro
1               5                   10                  15

Ser Ser Ile Met Gly Arg Thr Ile Ala Phe Arg Val Leu Phe Cys Arg
            20                  25                  30

Ser Met Ser Gln Leu Arg Arg Asp Leu Phe Arg Phe Leu Leu His Trp
        35                  40                  45

Phe Leu Arg Phe Lys Leu Thr Val Ser Pro Val Ser Trp Phe His
    50                  55                  60

Pro Arg Asn Pro Gln Gly Ile Leu Ala Val Val Thr Ile Ile Ala Phe
65                  70                  75                  80

Val Leu Lys Arg Tyr Thr Asn Val Lys Ile Lys Ala Glu Met Ala Tyr
                85                  90                  95
```

-continued

```
Arg Arg Lys Phe Trp Arg Asn Met Met Arg Thr Ala Leu Thr Tyr Glu
            100                 105                 110

Glu Trp Ala His Ala Ala Lys Met Leu Glu Lys Glu Thr Pro Lys Met
        115                 120                 125

Asn Glu Ser Asp Leu Tyr Asp Glu Leu Val Lys Asn Lys Leu Gln
130                 135                 140

Glu Leu Arg His Arg Arg Gln Glu Gly Ser Leu Arg Asp Ile Met Phe
145                 150                 155                 160

Cys Met Arg Ala Asp Leu Val Arg Asn Leu Gly Asn Met Cys Asn Ser
                165                 170                 175

Glu Leu His Lys Gly Arg Leu Gln Val Pro Arg His Ile Lys Glu Tyr
            180                 185                 190

Ile Asp Glu Val Ser Thr Gln Leu Arg Met Val Cys Asn Ser Asp Ser
        195                 200                 205

Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Gly Ala Ser Leu
225                 230                 235                 240

Gly Ala Phe His Val Gly Val Val Arg Thr Leu Val Glu His Lys Leu
                245                 250                 255

Leu Pro Arg Ile Ile Ala Gly Ser Ser Val Gly Ser Ile Ile Cys Ala
            260                 265                 270

Val Val Ala Ser Arg Ser Trp Pro Glu Leu Gln Ser Phe Phe Glu Asn
        275                 280                 285

Ser Leu His Ser Leu Gln Phe Phe Asp Gln Leu Gly Gly Val Phe Ser
    290                 295                 300

Ile Val Lys Arg Val Met Thr Gln Gly Ala Leu His Asp Ile Arg Gln
305                 310                 315                 320

Leu Gln Cys Met Leu Arg Asn Leu Thr Ser Asn Leu Thr Phe Gln Glu
                325                 330                 335

Ala Tyr Asp Met Thr Gly Arg Ile Leu Gly Ile Thr Val Cys Ser Pro
            340                 345                 350

Arg Lys His Glu Pro Pro Arg Cys Leu Asn Tyr Leu Thr Ser Pro His
        355                 360                 365

Val Val Ile Trp Ser Ala Val Thr Ala Ser Cys Ala Phe Pro Gly Leu
    370                 375                 380

Phe Glu Ala Gln Glu Leu Met Ala Lys Asp Arg Ser Gly Glu Ile Val
385                 390                 395                 400

Pro Tyr His Pro Pro Phe Asn Leu Asp Pro Glu Val Gly Thr Lys Ser
                405                 410                 415

Ser Ser Gly Arg Arg Trp Arg Asp Gly Ser Leu Glu Val Asp Leu Pro
            420                 425                 430

Met Met Gln Leu Lys Glu Leu Phe Asn Val Asn His Phe Ile Val Ser
        435                 440                 445

Gln Ala Asn Pro His Ile Ala Pro Leu Leu Arg Leu Lys Asp Leu Val
    450                 455                 460

Arg Ala Tyr Gly Gly Arg Phe Ala Ala Lys Leu Ala His Leu Val Glu
465                 470                 475                 480

Met Glu Val Lys His Arg Cys Asn Gln Val Leu Glu Leu Gly Phe Pro
                485                 490                 495

Leu Gly Gly Leu Ala Lys Leu Phe Ala Gln Glu Trp Glu Gly Asp Val
            500                 505                 510

Thr Val Val Met Pro Ala Thr Leu Ala Gln Tyr Ser Lys Ile Ile Gln
        515                 520                 525
```

Asn Pro Thr His Val Glu Leu Gln Lys Ala Ala Asn Gln Gly Arg Arg
            530                 535                 540

Cys Thr Trp Glu Lys Leu Ser Ala Ile Lys Ser Asn Cys Gly Ile Glu
545                 550                 555                 560

Leu Ala Leu Asp Asp Ser Val Ala Ile Leu Asn His Met Arg Arg Leu
                565                 570                 575

Lys Lys Ser Ala Glu Arg Ala Thr Ala Thr Ser Ser Ser His His
            580                 585                 590

Gly Leu Ala Ser Thr Thr Arg Phe Asn Ala Ser Arg Arg Ile Pro Ser
            595                 600                 605

Trp Asn Val Leu Ala Arg Glu Asn Ser Thr Gly Ser Leu Asp Asp Leu
610                 615                 620

Val Thr Asp Asn Asn Leu His Ala Ser Ser Gly Arg Asn Leu Ser Asp
625                 630                 635                 640

Ser Glu Thr Glu Ser Val Glu Leu Ser Ser Trp Thr Arg Thr Gly Gly
                645                 650                 655

Pro Leu Met Arg Thr Ala Ser Ala Asn Lys Phe Ile Asp Phe Val Gln
            660                 665                 670

Ser Leu Asp Ile Asp Ile Ala Leu Val Arg Gly Phe Ser Ser Ser Pro
            675                 680                 685

Asn Ser Pro Ala Val Pro Pro Gly Gly Ser Phe Thr Pro Ser Pro Arg
690                 695                 700

Ser Ile Ala Ala His Ser Asp Ile Glu Ser Asn Ser Asn Ser Asn Asn
705                 710                 715                 720

Leu Gly Thr Ser Thr Ser Ser Ile Thr Val Thr Glu Gly Asp Leu Leu
                725                 730                 735

Gln Pro Glu Arg Thr Ser Asn Gly Phe Val Leu Asn Val Val Lys Arg
            740                 745                 750

Glu Asn Leu Gly Met Pro Ser Ile Gly Asn Gln Asn Thr Glu Leu Pro
            755                 760                 765

Glu Ser Val Gln Leu Asp Ile Pro Glu Lys Glu Met Asp Cys Ser Ser
770                 775                 780

Val Ser Glu His Glu Glu Asp Asp Asn Asp Asn Glu Glu His Asn
785                 790                 795                 800

Gly Ser Ser Leu Val Thr Val Ser Ser Glu Asp Ser Gly Leu Gln Glu
                805                 810                 815

Pro Val Ser Gly Ser Val Ile Asp Ala
            820                 825

<210> SEQ ID NO 4
<211> LENGTH: 1870
<212> TYPE: DNA
<213> ORGANISM: Arabidopsis thaliana

<400> SEQUENCE: 4
ctaaagccat ggatgatgct ggtaaaatca cttccacaag ccatctcata gtgagcccag        60
atgaaggaac ctttttggac ctgttcaagc acattgtgct gagtgatttg ggcagtggag       120
ccaaattctt tagggcttca gatcagagag tgcctgctac ggcagcatat tatagcaggt       180
ggcctgtttc agttttcatt tgcaaaatac ttcaactttt ccagatgcca gccgcgatgc       240
ttggtcatct tactgatttc ttgctcaact tctattatca gaatcatggc ttccttggca       300
tactcagaaa catcttctta ataagactga agataccaaa aagaggtgaa gccgacttta       360
taagcacgat agggtattta gattcacgaa tggaccttca cgggacgcca atggtgtcgc       420

```
accaggcaga cgaagtgatt tcaaatgcag ataatccaag cctgaaagaa gggcacaatt    480
caaagataaa aggagcccctt gggaaccgat ctctcatgga tctttgtatc atggcgtcaa    540
agcttgctta tgaaaatacc aaagttgttg aaagagtagt tgccgaacat tggaagatgc    600
atttcgtggc tgactatggg ggcatgaatt atttccaaga tgcaaggaac actcatgcgt    660
tcatcttttg tgacaagcca aaagatgcaa acttgatagt gatcagcttc agaggcacag    720
gaccttttag tataccaaat tggtgtactg attttgattt ctccttagtt gggttgggag    780
acgcaggaag tgtccatgtt ggattcttag aagcaatggg tttgggtcac agaaattcta    840
tttccagctt tgagactagc attaacacaa agtcgccagg aagcataacc gaattaagga    900
aagagtccga gatggctccg gaccacttgg tatgggcata tgatggtgtt tactttcttg    960
cggcatcgac gctcaaggga ttactaaaag accacaagaa cgcaaaattt gtagtcactg   1020
ggcatagctt aggtggtgca cttgctatac tgttcacatg cattcttgag atacagcagg   1080
agacagaggt gcttgacaga ctgctaaatg tatacacatt cggacagcct aggattggga   1140
actataatct tggttacttc atgcagaacc gtctcaattt tccagaacgt aggtatttca   1200
gggtggttta ctgcaatgac atggttccta gggtgccttt cgatgatgtc ttcttcactt   1260
tcgagcattt cggaacctgc atttactatg atagccgctt ctttggctac tttaccaaag   1320
aggagcccag cagaaaccct ttcggaatag aaaatgccat cagtgcgcac atcaccgcct   1380
ggtgggagct ctggagaagt ttcatattaa atcacgtata tggcgcagaa tacaaggaga   1440
cctgggaatc cagaatgttc aggatatgg gactgtttct ccctggtgtt gcagctcata   1500
gtcctgtgaa ttatgtcaat tctgtcaggc ttggaaggga gcttgcaatt ccccttgatgt   1560
ctctgaaaat gatggcacaa ggttactaga attatcgtta taaagtctaa gagatgatca   1620
ttaatgataa atggttcact ctttgccaaa aaaagaaaaa taatcaaaag gcttacgcta   1680
ttgtaataaa aggatagctg tttcatgaac aggtcgccta gggttgtggt gtggagcttt   1740
gatatgcata tatgcatata tggcctgttt gtttgtcagt ttgttttttct ctttaaacaa   1800
aatgaaatgc ggtagttcaa taaaaaggaa cgttgagtag ttttttgggtt gccaaaaaaa   1860
aaaaaaaaaa                                                          1870
```

<210> SEQ ID NO 5
<211> LENGTH: 526
<212> TYPE: PRT
<213> ORGANISM: Arabidopsis thaliana

<400> SEQUENCE: 5

```
Met Asp Asp Ala Gly Lys Ile Thr Ser Thr Ser His Leu Ile Val Ser
1               5                   10                  15

Pro Asp Glu Gly Thr Phe Leu Asp Leu Phe Lys His Ile Val Leu Ser
            20                  25                  30

Asp Leu Gly Ser Gly Ala Lys Phe Phe Arg Ala Ser Asp Gln Arg Val
        35                  40                  45

Pro Ala Thr Ala Ala Tyr Tyr Ser Arg Trp Pro Val Ser Val Phe Ile
    50                  55                  60

Cys Lys Ile Leu Gln Leu Phe Gln Met Pro Ala Ala Met Leu Gly His
65                  70                  75                  80

Leu Thr Asp Phe Leu Leu Asn Pro Tyr Tyr Gln Asn His Gly Phe Leu
                85                  90                  95

Gly Ile Leu Arg Asn Ile Phe Leu Ile Arg Leu Lys Ile Pro Lys Arg
            100                 105                 110

Gly Glu Ala Asp Phe Ile Ser Thr Ile Gly Tyr Leu Asp Ser Arg Met
```

```
                    115                 120                 125
Asp Leu His Gly Thr Pro Met Val Ser His Gln Ala Asp Glu Val Ile
130                 135                 140

Ser Asn Ala Asp Asn Pro Ser Leu Lys Glu Gly His Asn Ser Lys Ile
145                 150                 155                 160

Lys Gly Ala Leu Gly Asn Arg Ser Leu Met Asp Leu Cys Ile Met Ala
                165                 170                 175

Ser Lys Leu Ala Tyr Glu Asn Thr Lys Val Val Glu Arg Val Val Ala
                180                 185                 190

Glu His Trp Lys Met His Phe Val Ala Asp Tyr Gly Gly Met Asn Tyr
            195                 200                 205

Phe Gln Asp Ala Arg Asn Thr His Ala Phe Ile Phe Cys Asp Lys Pro
        210                 215                 220

Lys Asp Ala Asn Leu Ile Val Ile Ser Phe Arg Gly Thr Gly Pro Phe
225                 230                 235                 240

Ser Ile Pro Asn Trp Cys Thr Asp Phe Asp Phe Ser Leu Val Gly Leu
                245                 250                 255

Gly Asp Ala Gly Ser Val His Val Gly Phe Leu Glu Ala Met Gly Leu
                260                 265                 270

Gly His Arg Asn Ser Ile Ser Ser Phe Glu Thr Ser Ile Asn Thr Lys
            275                 280                 285

Ser Pro Gly Ser Ile Thr Glu Leu Arg Lys Glu Ser Glu Met Ala Pro
        290                 295                 300

Asp His Leu Val Trp Ala Tyr Asp Gly Val Tyr Phe Leu Ala Ala Ser
305                 310                 315                 320

Thr Leu Lys Gly Leu Leu Lys Asp His Lys Asn Ala Lys Phe Val Val
                325                 330                 335

Thr Gly His Ser Leu Gly Gly Ala Leu Ala Ile Leu Phe Thr Cys Ile
                340                 345                 350

Leu Glu Ile Gln Gln Glu Thr Glu Val Leu Asp Arg Leu Leu Asn Val
            355                 360                 365

Tyr Thr Phe Gly Gln Pro Arg Ile Gly Asn Tyr Asn Leu Gly Tyr Phe
        370                 375                 380

Met Gln Asn Arg Leu Asn Phe Pro Glu Arg Arg Tyr Phe Arg Val Val
385                 390                 395                 400

Tyr Cys Asn Asp Met Val Pro Arg Val Pro Phe Asp Asp Val Phe Phe
                405                 410                 415

Thr Phe Glu His Phe Gly Thr Cys Ile Tyr Tyr Asp Ser Arg Phe Phe
                420                 425                 430

Gly Tyr Phe Thr Lys Glu Glu Pro Ser Arg Asn Pro Phe Gly Ile Glu
            435                 440                 445

Asn Ala Ile Ser Ala His Ile Thr Ala Trp Trp Glu Leu Trp Arg Ser
        450                 455                 460

Phe Ile Leu Asn His Val Tyr Gly Ala Glu Tyr Lys Glu Thr Trp Glu
465                 470                 475                 480

Ser Arg Met Phe Arg Ile Leu Gly Leu Phe Leu Pro Gly Val Ala Ala
                485                 490                 495

His Ser Pro Val Asn Tyr Val Asn Ser Val Arg Leu Gly Arg Glu Leu
                500                 505                 510

Ala Ile Pro Leu Met Ser Leu Lys Met Met Ala Gln Gly Tyr
            515                 520                 525

<210> SEQ ID NO 6
<211> LENGTH: 1900
```

```
<212> TYPE: DNA
<213> ORGANISM: Arabidopsis thaliana

<400> SEQUENCE: 6
gatcttcaaa gtagttttga actctctgct gagggaaaaa aagagtgagg gaagtgagaa      60
accaaaagcc atggctgctt ctgctactac tagcaataat attgctccaa acttcttggt     120
tgttgaccca aaaagggaa gaaaagaga catattcaag tatttggtga ggaaagatgt      180
gaagagtgga atgagtttct tggatagttc agaggaagga gttaaaggtg gcgcagcagt     240
tgatcatagg tggattttat tggtttctat catcattcgg agggttcttg cgcttattga     300
taccccatta aagtaccttg gatatgtcat tgatttcttt ctcaaccttta tctcccaaaa     360
tagtggattc tctggcatac tcaacaactt tctccatgga aacctgaaga taccgaggag     420
aggaacagag aattttataa gcacgattgg gcaattggat gggcgaatag acctttatag     480
aactacaata ttatcggaga agtagatga ttctgttgct actgatgtta caacattaa       540
agcagaactg ggtaatcgat atctcatgga tctttgtatc atggcagcca aacttgtcta     600
tgagaatgag aaagttgctc aaaatgttgt tgatcgtcac tggaagatgc attttgtggc     660
tttctacaac tgctggaatg agtaccaaaa gcaaacaac acccaagtgt tcatatgttg      720
tgacaagcca aaggatgcaa atttgatagt ggtcagcttt agaggaacag aaccatttaa     780
tgcacaagat tggagtacgg attttgattt ctcgtggtat gaaatcccaa aagttggaaa     840
gatccatatt ggattcttag aagctttagg tctgggcaac agaagtgacg ctaccacttt     900
ccaaactcac cttcagagga acatacagg tttcttccat ctaaatggtg agtctgaagg      960
caatatgacg gaatgggcaa agaagagtgc atactatgct gtcgcgttga agctaaagag    1020
cttactgaaa gaacacagga atgctaaatt tatagtcact ggacatagtt taggtggagc    1080
acttgcaata ttgttcccgt caatactggt tatacaggag gagacagaga tgctaaacag    1140
gttgctgaac atatacacat ttgggcagcc aagaattgga gatgcacagc ttggaacttt    1200
catggagtcc cacttgaatt atccagttac tagatacttc agggttgttt actgcaacga    1260
tatggtgcct agagtgcctt tcgatgacaa gattttcgct ttcaagcatt tcggtacatg    1320
tctttactat gatagccgct acttttggccg atttatggat gaggagccga acagaaatta    1380
ttttggactg agacacataa ttccaatgcg ggtgaatgca ttatgggaac tattcagaag    1440
ttttatgata acccatgcac atggacctga ctaccaggag agttggttct gcactctttc    1500
cagggtagca ggactggtgc ttcctggtgt tgctgctcat agtcctatag attatgttaa    1560
ttcagttagg cttggaaagg agagagtagc tccaatgaca tccttgaaaa gcttcgctcg    1620
caagtcataa atctgggttg cacttgtact cttcttcatg gatgagacac tgaacacaaa    1680
ggaaaataat aacagggtgc agtttaaaat gatcataagg gaaataaatc ttatatttct    1740
tactcttacg gaaatttgat aatctgtgac cttgtggttg tgggtagttc caatttaatt    1800
tcttttctt ttcaataaaa atcctgtact tcggtgataa tatgaattat agtgtgactt    1860
ttttggttgc ccatagaaaa aaaaaaaaaa aaaaaaaaa                            1900

<210> SEQ ID NO 7
<211> LENGTH: 519
<212> TYPE: PRT
<213> ORGANISM: Arabidopsis thaliana

<400> SEQUENCE: 7

Met Ala Ala Ser Ala Thr Thr Ser Asn Asn Ile Ala Pro Asn Phe Leu
1               5                   10                  15
```

```
Val Val Asp Pro Lys Lys Gly Arg Lys Arg Asp Ile Phe Lys Tyr Leu
         20              25              30
Val Arg Lys Asp Val Lys Ser Gly Met Ser Phe Leu Asp Ser Ser Glu
         35              40              45
Glu Gly Val Lys Gly Gly Ala Ala Val Asp His Arg Trp Ile Leu Leu
 50              55              60
Val Ser Ile Ile Arg Arg Val Leu Ala Leu Ile Asp Thr Pro Leu
 65              70              75              80
Lys Tyr Leu Gly Tyr Val Ile Asp Phe Phe Leu Asn Leu Ile Ser Gln
                 85              90              95
Asn Ser Gly Phe Ser Gly Ile Leu Asn Asn Phe Leu His Gly Asn Leu
             100             105             110
Lys Ile Pro Arg Arg Gly Thr Glu Asn Phe Ile Ser Thr Ile Gly Gln
         115             120             125
Leu Asp Gly Arg Ile Asp Leu Tyr Arg Thr Thr Ile Leu Ser Glu Lys
         130             135             140
Val Asp Asp Ser Val Ala Thr Asp Val Asn Asn Ile Lys Ala Glu Leu
145             150             155             160
Gly Asn Arg Tyr Leu Met Asp Leu Cys Ile Met Ala Ala Lys Leu Val
                 165             170             175
Tyr Glu Asn Glu Lys Val Ala Gln Asn Val Val Asp Arg His Trp Lys
             180             185             190
Met His Phe Val Ala Phe Tyr Asn Cys Trp Asn Glu Tyr Gln Lys Gln
         195             200             205
Asn Asn Thr Gln Val Phe Ile Cys Cys Asp Lys Pro Lys Asp Ala Asn
210             215             220
Leu Ile Val Val Ser Phe Arg Gly Thr Glu Pro Phe Asn Ala Gln Asp
225             230             235             240
Trp Ser Thr Asp Phe Asp Phe Ser Trp Tyr Glu Ile Pro Lys Val Gly
                 245             250             255
Lys Ile His Ile Gly Phe Leu Glu Ala Leu Gly Leu Gly Asn Arg Ser
             260             265             270
Asp Ala Thr Thr Phe Gln Thr His Leu Gln Arg Lys His Thr Gly Phe
         275             280             285
Phe His Leu Asn Gly Glu Ser Glu Gly Asn Met Thr Glu Trp Ala Lys
         290             295             300
Lys Ser Ala Tyr Tyr Ala Val Ala Leu Lys Leu Lys Ser Leu Leu Lys
305             310             315             320
Glu His Arg Asn Ala Lys Phe Ile Val Thr Gly His Ser Leu Gly Gly
                 325             330             335
Ala Leu Ala Ile Leu Phe Pro Ser Ile Leu Val Ile Gln Glu Glu Thr
             340             345             350
Glu Met Leu Asn Arg Leu Leu Asn Ile Tyr Thr Phe Gly Gln Pro Arg
         355             360             365
Ile Gly Asp Ala Gln Leu Gly Thr Phe Met Glu Ser His Leu Asn Tyr
         370             375             380
Pro Val Thr Arg Tyr Phe Arg Val Tyr Cys Asn Asp Met Val Pro
385             390             395             400
Arg Val Pro Phe Asp Asp Lys Ile Phe Ala Phe Lys His Phe Gly Thr
                 405             410             415
Cys Leu Tyr Tyr Asp Ser Arg Tyr Phe Gly Arg Phe Met Asp Glu Glu
             420             425             430
Pro Asn Arg Asn Tyr Phe Gly Leu Arg His Ile Ile Pro Met Arg Val
         435             440             445
```

```
Asn Ala Leu Trp Glu Leu Phe Arg Ser Phe Met Ile Thr His Ala His
    450                 455                 460

Gly Pro Asp Tyr Gln Glu Ser Trp Phe Cys Thr Leu Ser Arg Val Ala
465                 470                 475                 480

Gly Leu Val Leu Pro Gly Val Ala Ala His Ser Pro Ile Asp Tyr Val
                485                 490                 495

Asn Ser Val Arg Leu Gly Lys Glu Arg Val Ala Pro Met Thr Ser Leu
            500                 505                 510

Lys Ser Phe Ala Arg Lys Ser
        515

<210> SEQ ID NO 8
<211> LENGTH: 825
<212> TYPE: PRT
<213> ORGANISM: Arabidopsis thaliana

<400> SEQUENCE: 8

Met Asp Ile Ser Asn Glu Ala Ser Val Asp Pro Phe Ser Ile Gly Pro
1               5                   10                  15

Ser Ser Ile Met Gly Arg Thr Ile Ala Phe Arg Val Leu Phe Cys Arg
            20                  25                  30

Ser Met Ser Gln Leu Arg Arg Asp Leu Phe Arg Phe Leu Leu His Trp
        35                  40                  45

Phe Leu Arg Phe Lys Leu Thr Val Ser Pro Val Ser Trp Phe His
50                  55                  60

Pro Arg Asn Pro Gln Gly Ile Leu Ala Val Val Thr Ile Ile Ala Phe
65                  70                  75                  80

Val Leu Lys Arg Tyr Thr Asn Val Lys Ile Lys Ala Glu Met Ala Tyr
                85                  90                  95

Arg Arg Lys Phe Trp Arg Asn Met Met Arg Thr Ala Leu Thr Tyr Glu
                100                 105                 110

Glu Trp Ala His Ala Ala Lys Met Leu Glu Lys Glu Thr Pro Lys Met
            115                 120                 125

Asn Glu Ser Asp Leu Tyr Asp Glu Glu Leu Val Lys Asn Lys Leu Gln
    130                 135                 140

Glu Leu Arg His Arg Arg Gln Glu Gly Ser Leu Arg Asp Ile Met Phe
145                 150                 155                 160

Cys Met Arg Ala Asp Leu Val Arg Asn Leu Gly Asn Met Cys Asn Ser
                165                 170                 175

Glu Leu His Lys Gly Arg Leu Gln Pro Arg His Ile Lys Glu Tyr
            180                 185                 190

Ile Asp Glu Val Ser Thr Gln Leu Arg Met Val Cys Asn Ser Asp Ser
        195                 200                 205

Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Gly Ala Ser Leu
225                 230                 235                 240

Asp Ala Phe His Val Gly Val Val Arg Thr Leu Val Glu His Lys Leu
                245                 250                 255

Leu Pro Arg Ile Ile Ala Gly Ser Ser Val Gly Ser Ile Ile Cys Ala
                260                 265                 270

Val Val Ala Ser Arg Ser Trp Pro Glu Leu Gln Ser Phe Phe Glu Asn
            275                 280                 285

Ser Leu His Ser Leu Gln Phe Phe Asp Gln Leu Gly Gly Val Phe Ser
    290                 295                 300
```

-continued

```
Ile Val Lys Arg Val Met Thr Gln Gly Ala Leu His Asp Ile Arg Gln
305                 310                 315                 320

Leu Gln Cys Met Leu Arg Asn Leu Thr Ser Asn Leu Thr Phe Gln Glu
            325                 330                 335

Ala Tyr Asp Met Thr Gly Arg Ile Leu Gly Ile Thr Val Cys Ser Pro
            340                 345                 350

Arg Lys His Glu Pro Pro Arg Cys Leu Asn Tyr Leu Thr Ser Pro His
            355                 360                 365

Val Val Ile Trp Ser Ala Val Thr Ala Ser Cys Ala Phe Pro Gly Leu
            370                 375                 380

Phe Glu Ala Gln Glu Leu Met Ala Lys Asp Arg Ser Gly Glu Ile Val
385                 390                 395                 400

Pro Tyr His Pro Pro Phe Asn Leu Asp Pro Glu Val Gly Thr Lys Ser
            405                 410                 415

Ser Ser Gly Arg Arg Trp Arg Asp Gly Ser Leu Glu Val Asp Leu Pro
            420                 425                 430

Met Met Gln Leu Lys Glu Leu Phe Asn Val Asn His Phe Ile Val Ser
            435                 440                 445

Gln Ala Asn Pro His Ile Ala Pro Leu Leu Arg Leu Lys Asp Leu Val
450                 455                 460

Arg Ala Tyr Gly Gly Arg Phe Ala Ala Lys Leu Ala His Leu Val Glu
465                 470                 475                 480

Met Glu Val Lys His Arg Cys Asn Gln Val Leu Glu Leu Gly Phe Pro
            485                 490                 495

Leu Gly Gly Leu Ala Lys Leu Phe Ala Gln Glu Trp Glu Gly Asp Val
            500                 505                 510

Thr Val Val Met Pro Ala Thr Leu Ala Gln Tyr Ser Lys Ile Ile Gln
            515                 520                 525

Asn Pro Thr His Val Glu Leu Gln Lys Ala Ala Asn Gln Gly Arg Arg
            530                 535                 540

Cys Thr Trp Glu Lys Leu Ser Ala Ile Lys Ser Asn Cys Gly Ile Glu
545                 550                 555                 560

Leu Ala Leu Asp Asp Ser Val Ala Ile Leu Asn His Met Arg Arg Leu
            565                 570                 575

Lys Lys Ser Ala Glu Arg Ala Ala Thr Ala Thr Ser Ser His His
            580                 585                 590

Gly Leu Ala Ser Thr Thr Arg Phe Asn Ala Ser Arg Arg Ile Pro Ser
            595                 600                 605

Trp Asn Val Leu Ala Arg Glu Asn Ser Thr Gly Ser Leu Asp Asp Leu
            610                 615                 620

Val Thr Asp Asn Asn Leu His Ala Ser Ser Gly Arg Asn Leu Ser Asp
625                 630                 635                 640

Ser Glu Thr Glu Ser Val Glu Leu Ser Ser Trp Thr Arg Thr Gly Gly
            645                 650                 655

Pro Leu Met Arg Thr Ala Ser Ala Asn Lys Phe Ile Asp Phe Val Gln
            660                 665                 670

Ser Leu Asp Ile Asp Ile Ala Leu Val Arg Gly Phe Ser Ser Ser Pro
            675                 680                 685

Asn Ser Pro Ala Val Pro Pro Gly Gly Ser Phe Thr Pro Ser Pro Arg
            690                 695                 700

Ser Ile Ala Ala His Ser Asp Ile Glu Ser Asn Ser Asn Ser Asn Asn
705                 710                 715                 720

Leu Gly Thr Ser Thr Ser Ser Ile Thr Val Thr Glu Gly Asp Leu Leu
```

```
                          725                 730                 735
Gln Pro Glu Arg Thr Ser Asn Gly Phe Val Leu Asn Val Lys Arg
                740                 745                 750
Glu Asn Leu Gly Met Pro Ser Ile Gly Asn Gln Asn Thr Glu Leu Pro
            755                 760                 765
Glu Ser Val Gln Leu Asp Ile Pro Glu Lys Glu Met Asp Cys Ser Ser
            770                 775                 780
Val Ser Glu His Glu Glu Asp Asn Asp Asn Glu Glu His Asn
785                 790                 795                 800
Gly Ser Ser Leu Val Thr Val Ser Ser Glu Asp Ser Gly Leu Gln Glu
                805                 810                 815
Pro Val Ser Gly Ser Val Ile Asp Ala
            820                 825

<210> SEQ ID NO 9
<211> LENGTH: 825
<212> TYPE: PRT
<213> ORGANISM: Arabidopsis thaliana

<400> SEQUENCE: 9

Met Asp Ile Ser Asn Glu Ala Ser Val Asp Pro Phe Ser Ile Gly Pro
1               5                   10                  15
Ser Ser Ile Met Gly Arg Thr Ile Ala Phe Arg Val Leu Phe Cys Arg
            20                  25                  30
Ser Met Ser Gln Leu Arg Arg Asp Leu Phe Arg Phe Leu Leu His Trp
        35                  40                  45
Phe Leu Arg Phe Lys Leu Thr Val Ser Pro Phe Val Ser Trp Phe His
    50                  55                  60
Pro Arg Asn Pro Gln Gly Ile Leu Ala Val Val Thr Ile Ile Ala Phe
65                  70                  75                  80
Val Leu Lys Arg Tyr Thr Asn Val Lys Ile Lys Ala Glu Met Ala Tyr
                85                  90                  95
Arg Arg Lys Phe Trp Arg Asn Met Met Arg Thr Ala Leu Thr Tyr Glu
            100                 105                 110
Glu Trp Ala His Ala Ala Lys Met Leu Glu Lys Glu Thr Pro Lys Met
        115                 120                 125
Asn Glu Ser Asp Leu Tyr Asp Glu Glu Leu Val Lys Asn Lys Leu Gln
    130                 135                 140
Glu Leu Arg His Arg Gln Glu Gly Ser Leu Arg Asp Ile Met Phe
145                 150                 155                 160
Cys Met Arg Ala Asp Leu Val Arg Asn Leu Gly Asn Met Cys Asn Ser
                165                 170                 175
Glu Leu His Lys Gly Arg Leu Gln Val Pro Arg His Ile Lys Glu Tyr
            180                 185                 190
Ile Asp Glu Val Ser Thr Gln Leu Arg Met Val Cys Asn Ser Asp Ser
        195                 200                 205
Glu Glu Leu Ser Leu Glu Glu Lys Leu Ser Phe Met His Glu Thr Arg
    210                 215                 220
His Ala Phe Gly Arg Thr Ala Leu Leu Leu Ser Gly Gly Ala Ser Leu
225                 230                 235                 240
Gly Ala Phe His Val Gly Val Val Arg Thr Leu Val Glu His Lys Leu
                245                 250                 255
Leu Pro Arg Ile Ile Ala Gly Ser Ser Val Gly Ser Ile Ile Cys Ala
            260                 265                 270
Val Val Ala Ser Arg Ser Trp Pro Glu Leu Gln Ser Phe Phe Glu Asn
```

```
                275                 280                 285
Ser Leu His Ser Leu Gln Phe Phe Asp Gln Leu Gly Gly Val Phe Ser
290                 295                 300

Ile Val Lys Arg Val Met Thr Gln Gly Ala Leu His Asp Ile Arg Gln
305                 310                 315                 320

Leu Gln Cys Met Leu Arg Asn Leu Thr Ser Asn Leu Thr Phe Gln Glu
                325                 330                 335

Ala Tyr Asp Met Thr Gly Arg Ile Leu Gly Ile Thr Val Cys Ser Pro
                340                 345                 350

Arg Lys His Glu Pro Pro Arg Cys Leu Asn Tyr Leu Thr Ser Pro His
                355                 360                 365

Val Val Ile Trp Ser Ala Val Thr Ala Ser Cys Ala Phe Pro Gly Leu
            370                 375                 380

Phe Glu Ala Gln Glu Leu Met Ala Lys Asp Arg Ser Gly Glu Ile Val
385                 390                 395                 400

Pro Tyr His Pro Pro Phe Asn Leu Asp Pro Glu Val Gly Thr Lys Ser
                405                 410                 415

Ser Ser Gly Arg Arg Trp Arg Asp Gly Ser Leu Glu Val Asp Leu Pro
                420                 425                 430

Met Met Gln Leu Lys Lys Leu Phe Asn Val Asn His Phe Ile Val Ser
                435                 440                 445

Gln Ala Asn Pro His Ile Ala Pro Leu Leu Arg Leu Lys Asp Leu Val
            450                 455                 460

Arg Ala Tyr Gly Gly Arg Phe Ala Ala Lys Leu Ala His Leu Val Glu
465                 470                 475                 480

Met Glu Val Lys His Arg Cys Asn Gln Val Leu Glu Leu Gly Phe Pro
                485                 490                 495

Leu Gly Gly Leu Ala Lys Leu Phe Ala Gln Glu Trp Glu Gly Asp Val
                500                 505                 510

Thr Val Val Met Pro Ala Thr Leu Ala Gln Tyr Ser Lys Ile Ile Gln
            515                 520                 525

Asn Pro Thr His Val Glu Leu Gln Lys Ala Ala Asn Gln Gly Arg Arg
            530                 535                 540

Cys Thr Trp Glu Lys Leu Ser Ala Ile Lys Ser Asn Cys Gly Ile Glu
545                 550                 555                 560

Leu Ala Leu Asp Asp Ser Val Ala Ile Leu Asn His Met Arg Arg Leu
                565                 570                 575

Lys Lys Ser Ala Glu Arg Ala Thr Ala Thr Ser Ser Ser His His
            580                 585                 590

Gly Leu Ala Ser Thr Thr Arg Phe Asn Ala Ser Arg Arg Ile Pro Ser
                595                 600                 605

Trp Asn Val Leu Ala Arg Glu Asn Ser Thr Gly Ser Leu Asp Asp Leu
            610                 615                 620

Val Thr Asp Asn Asn Leu His Ala Ser Ser Gly Arg Asn Leu Ser Asp
625                 630                 635                 640

Ser Glu Thr Glu Ser Val Glu Leu Ser Ser Trp Thr Arg Thr Gly Gly
                645                 650                 655

Pro Leu Met Arg Thr Ala Ser Ala Asn Lys Phe Ile Asp Phe Val Gln
                660                 665                 670

Ser Leu Asp Ile Asp Ile Ala Leu Val Arg Gly Phe Ser Ser Ser Pro
            675                 680                 685

Asn Ser Pro Ala Val Pro Pro Gly Gly Ser Phe Thr Pro Ser Pro Arg
            690                 695                 700
```

```
Ser Ile Ala Ala His Ser Asp Ile Glu Ser Asn Ser Asn Ser Asn Asn
705                 710                 715                 720

Leu Gly Thr Ser Thr Ser Ile Thr Val Thr Glu Gly Asp Leu Leu
            725                 730                 735

Gln Pro Glu Arg Thr Ser Asn Gly Phe Val Leu Asn Val Val Lys Arg
            740                 745                 750

Glu Asn Leu Gly Met Pro Ser Ile Gly Asn Gln Asn Thr Glu Leu Pro
            755                 760                 765

Glu Ser Val Gln Leu Asp Ile Pro Glu Lys Glu Met Asp Cys Ser Ser
            770                 775                 780

Val Ser Glu His Glu Glu Asp Asn Asp Asn Glu Glu Glu His Asn
785                 790                 795                 800

Gly Ser Ser Leu Val Thr Val Ser Ser Glu Asp Ser Gly Leu Gln Glu
            805                 810                 815

Pro Val Ser Gly Ser Val Ile Asp Ala
            820                 825

<210> SEQ ID NO 10
<211> LENGTH: 825
<212> TYPE: PRT
<213> ORGANISM: Arabidopsis thaliana

<400> SEQUENCE: 10

Met Asp Ile Ser Asn Glu Ala Ser Val Asp Pro Phe Ser Ile Gly Pro
1               5                   10                  15

Ser Ser Ile Met Gly Arg Thr Ile Ala Phe Arg Val Leu Phe Cys Arg
            20                  25                  30

Ser Met Ser Gln Leu Arg Arg Asp Leu Phe Arg Phe Leu Leu His Trp
            35                  40                  45

Phe Leu Arg Phe Lys Leu Thr Val Ser Pro Phe Val Ser Trp Phe His
    50                  55                  60

Pro Arg Asn Pro Gln Gly Ile Leu Ala Val Val Thr Ile Ile Ala Phe
65                  70                  75                  80

Val Leu Lys Arg Tyr Thr Asn Val Lys Ile Lys Ala Glu Met Ala Tyr
            85                  90                  95

Arg Arg Lys Phe Trp Arg Asn Met Met Arg Thr Ala Leu Thr Tyr Glu
            100                 105                 110

Glu Trp Ala His Ala Ala Lys Met Leu Glu Lys Glu Thr Pro Lys Met
            115                 120                 125

Asn Glu Ser Asp Leu Tyr Asp Glu Glu Leu Val Lys Asn Lys Leu Gln
    130                 135                 140

Glu Leu Arg His Arg Arg Gln Glu Gly Ser Leu Arg Asp Ile Met Phe
145                 150                 155                 160

Cys Met Arg Ala Asp Leu Val Arg Asn Leu Gly Asn Met Cys Asn Ser
            165                 170                 175

Glu Leu His Lys Gly Arg Leu Gln Val Pro Arg His Ile Lys Glu Tyr
            180                 185                 190

Ile Asp Glu Val Ser Thr Gln Leu Arg Met Val Cys Asn Ser Asp Ser
            195                 200                 205

Glu Glu Leu Ser Leu Glu Glu Lys Leu Ser Phe Met His Glu Thr Arg
    210                 215                 220

His Ala Phe Gly Arg Thr Ala Leu Leu Leu Ser Gly Ala Ser Leu
225                 230                 235                 240

Gly Ala Phe His Val Gly Val Val Arg Thr Leu Val Glu His Lys Leu
            245                 250                 255
```

-continued

```
Leu Pro Arg Ile Ile Ala Gly Ser Ser Val Gly Ser Ile Ile Cys Ala
            260                 265                 270

Val Val Ala Ser Arg Ser Trp Pro Glu Leu Gln Ser Phe Phe Glu Asn
        275                 280                 285

Ser Leu His Ser Leu Gln Phe Phe Asp Gln Leu Gly Gly Val Phe Ser
    290                 295                 300

Ile Val Lys Arg Val Met Thr Gln Gly Ala Leu His Asp Ile Arg Gln
305                 310                 315                 320

Leu Gln Cys Met Leu Arg Asn Leu Thr Ser Asn Leu Thr Phe Gln Glu
                325                 330                 335

Ala Tyr Asp Met Thr Gly Arg Ile Leu Gly Ile Thr Val Cys Ser Pro
            340                 345                 350

Arg Lys His Glu Pro Pro Arg Cys Leu Asn Tyr Leu Thr Ser Pro His
        355                 360                 365

Val Val Ile Trp Ser Ala Val Thr Ala Ser Cys Ala Phe Pro Gly Leu
    370                 375                 380

Phe Glu Ala Gln Glu Leu Met Ala Lys Asp Arg Ser Gly Glu Ile Val
385                 390                 395                 400

Pro Tyr His Pro Pro Phe Asn Leu Asp Pro Glu Val Gly Thr Lys Ser
                405                 410                 415

Ser Ser Gly Arg Arg Trp Arg Asp Gly Ser Leu Glu Val Asp Leu Pro
            420                 425                 430

Met Met Gln Leu Lys Glu Leu Phe Asn Val Asn His Phe Ile Val Ser
        435                 440                 445

Gln Ala Asn Pro His Ile Ala Ser Leu Leu Arg Leu Lys Asp Leu Val
    450                 455                 460

Arg Ala Tyr Gly Gly Arg Phe Ala Ala Lys Leu Ala His Leu Val Glu
465                 470                 475                 480

Met Glu Val Lys His Arg Cys Asn Gln Val Leu Glu Leu Gly Phe Pro
                485                 490                 495

Leu Gly Gly Leu Ala Lys Leu Phe Ala Gln Glu Trp Glu Gly Asp Val
            500                 505                 510

Thr Val Val Met Pro Ala Thr Leu Ala Gln Tyr Ser Lys Ile Ile Gln
        515                 520                 525

Asn Pro Thr His Val Glu Leu Gln Lys Ala Ala Asn Gln Gly Arg Arg
    530                 535                 540

Cys Thr Trp Glu Lys Leu Ser Ala Ile Lys Ser Asn Cys Gly Ile Glu
545                 550                 555                 560

Leu Ala Leu Asp Asp Ser Val Ala Ile Leu Asn His Met Arg Arg Leu
                565                 570                 575

Lys Lys Ser Ala Glu Arg Ala Thr Ala Thr Ser Ser Ser His His
            580                 585                 590

Gly Leu Ala Ser Thr Thr Arg Phe Asn Ala Ser Arg Arg Ile Pro Ser
        595                 600                 605

Trp Asn Val Leu Ala Arg Glu Asn Ser Thr Gly Ser Leu Asp Asp Leu
    610                 615                 620

Val Thr Asp Asn Asn Leu His Ala Ser Ser Gly Arg Asn Leu Ser Asp
625                 630                 635                 640

Ser Glu Thr Glu Ser Val Glu Leu Ser Ser Trp Thr Arg Thr Gly Gly
                645                 650                 655

Pro Leu Met Arg Thr Ala Ser Ala Asn Lys Phe Ile Asp Phe Val Gln
            660                 665                 670

Ser Leu Asp Ile Asp Ile Ala Leu Val Arg Gly Phe Ser Ser Ser Pro
        675                 680                 685
```

```
Asn Ser Pro Ala Val Pro Pro Gly Gly Ser Phe Thr Pro Ser Pro Arg
    690                 695                 700
Ser Ile Ala Ala His Ser Asp Ile Glu Ser Asn Ser Asn Ser Asn Asn
705                 710                 715                 720
Leu Gly Thr Ser Thr Ser Ser Ile Thr Val Thr Glu Gly Asp Leu Leu
            725                 730                 735
Gln Pro Glu Arg Thr Ser Asn Gly Phe Val Leu Asn Val Val Lys Arg
        740                 745                 750
Glu Asn Leu Gly Met Pro Ser Ile Gly Asn Gln Asn Thr Glu Leu Pro
    755                 760                 765
Glu Ser Val Gln Leu Asp Ile Pro Glu Lys Glu Met Asp Cys Ser Ser
770                 775                 780
Val Ser Glu His Glu Glu Asp Asn Asp Asn Glu Glu Glu His Asn
785                 790                 795                 800
Gly Ser Ser Leu Val Thr Val Ser Ser Glu Asp Ser Gly Leu Gln Glu
            805                 810                 815
Pro Val Ser Gly Ser Val Ile Asp Ala
        820                 825

<210> SEQ ID NO 11
<211> LENGTH: 2478
<212> TYPE: DNA
<213> ORGANISM: Arabidopsis thaliana

<400> SEQUENCE: 11
```

| | | | | | |
|---|---|---|---|---|---|
| atggatataa | gtaatgaggc | tagtgtcgat | cccttttcga | ttggaccatc | atctatcatg | 60 |
| ggtcgaacca | ttgctttcag | agtcttgttc | tgtagatcaa | tgtcacagct | taggcgtgat | 120 |
| ctctttcggt | tcttgttgca | ttggtttctt | agatttaagc | tgaccgtttc | accgtttgtg | 180 |
| tcgtggtttc | atcctcggaa | ccctcaaggg | attttagcgg | tggttacaat | cattgccttt | 240 |
| gtgttgaaac | gatacacgaa | tgtgaaaata | aaggcgaaaa | tggcttaccg | gaggaagttt | 300 |
| tggaggaata | tgatgcggac | ggcttttgact | tatgaggaat | gggctcatgc | tgctaagatg | 360 |
| ttagagaagg | aaacaccaaa | gatgaatgaa | tctgatcttt | atgatgaaga | gttggttaag | 420 |
| aacaagcttc | aggagcttcg | tcatcgtcgc | caagaaggct | cacttagaga | cattatgttt | 480 |
| tgtatgagag | ctgatttggt | gaggaatctc | ggtaatatgt | gtaattcgga | gcttcataaa | 540 |
| ggtagacttc | aggttcctag | acatatcaaa | gagtacattg | atgaggtgtc | tactcagttg | 600 |
| agaatggttt | gtaactctga | ttcagaggag | ctttctttag | aagagaagct | ttcttttatg | 660 |
| catgaaacac | ggcatgcctt | tggtagaacg | gctttgctt | tgagtggtgg | ggcttctctt | 720 |
| gatgcgtttc | atgttggtgt | ggttaggact | tggttgagc | ataagctttt | acctcgaata | 780 |
| attgctggtt | ctagtgttgg | atccatcatt | tgtgctgttg | tggcctcaag | gtcttggcca | 840 |
| gaactacaga | gtttctttga | gaattctttg | cattctttac | agttctttga | tcagctcgga | 900 |
| ggcgtgttct | caatagtgaa | acgggtaatg | acacaagggg | ctctacacga | tatcagacag | 960 |
| ttgcaatgta | tgcttagaaa | cctcacaagc | aatctcacat | tccaagaagc | ttatgacatg | 1020 |
| acaggaagga | ttctcgggat | caccgtttgc | tccccaagaa | agcatgaacc | tcctcggtgt | 1080 |
| cttaactatt | tgacttcgcc | tcatgtggtt | atatggagcg | cagtgactgc | ttcttgtgct | 1140 |
| tttcctggtc | tctttgaagc | tcaagagcta | atggctaaag | atcgaagtgg | agagatcgta | 1200 |
| ccgtatcatc | cacctttcaa | tttggatcca | gaagtaggca | ctaaatcatc | atctggacgc | 1260 |
| cggtggagag | atggtagttt | ggaggttgat | ttaccaatga | tgcagcttaa | agaactgttc | 1320 |

| | |
|---|---|
| aatgtcaatc attttattgt gagccaagcc aatcctcaca ttgctccatt actgcgtcta | 1380 |
| aaggatttag ttcgagctta tggtggtaga ttcgcagcta agctcgcgca tctagtggag | 1440 |
| atggaggtca aacatagatg caaccaggta ttagagctcg gttttcctct cggtggactc | 1500 |
| gcaaagcttt ttgctcagga gtgggaaggt gatgttacag ttgtaatgcc tgctactctt | 1560 |
| gctcagtact cgaagattat acaaaatccg actcatgtcg agcttcagaa agcggctaac | 1620 |
| caaggaagaa gatgcacttg ggagaagctc tcagccataa aatcaaactg cgggatcgag | 1680 |
| cttgcgcttg atgattctgt agctattctt aaccatatgc ggaggctcaa gaaaagtgcg | 1740 |
| gagagagccg ccactgccac gtcttcgtct catcacggat tggcttcaac caccagattc | 1800 |
| aatgcttcaa gaagaatccc atcttggaac gtccttgcca gagagaactc aacaggctca | 1860 |
| ctggatgatc tagtcactga caataacctc cacgcttctt cgggcaggaa tttaagcgac | 1920 |
| agtgaaacag agagcgtgga gttgagttct tggacaagaa ctggtggacc tttaatgaga | 1980 |
| acagcttctg ctaataagtt cattgatttt gttcagagtc ttgatatcga cattgcattg | 2040 |
| gtcagaggat ttagtagcag tcccaattct ccagcagttc ctcctggtgg ctcgtttact | 2100 |
| ccaagcccga gatccatagc ggctcattcg gatatcgaat caaacagcaa tagcaacaat | 2160 |
| cttggaacaa gcacttcaag cataacagtt actgaaggtg atcttctaca gcctgagaga | 2220 |
| acgagtaacg gatttgtgtt aaacgtcgtt aaaagagaga acttgggaat gccatcgatt | 2280 |
| gggaaccaaa atacagagtt accagagagt gtacagctcg atataccgga gaaggagatg | 2340 |
| gattgtagct ctgtatcaga acacgaagaa gatgataacg acaatgaaga agaacataac | 2400 |
| ggctcgagtc tggttactgt ttcttcagaa gattccggtt tacaagaacc ggtgtctggt | 2460 |
| agtgttatag atgcttag | 2478 |

<210> SEQ ID NO 12
<211> LENGTH: 2478
<212> TYPE: DNA
<213> ORGANISM: Arabidopsis thaliana

<400> SEQUENCE: 12

| | |
|---|---|
| atggatataa gtaatgaggc tagtgtcgat ccctttttcga ttggaccatc atctatcatg | 60 |
| ggtcgaacca ttgcttttcag agtcttgttc tgtagatcaa tgtcacagct taggcgtgat | 120 |
| ctctttcggt tcttgttgca ttggtttctt agatttaagc tgaccgtttc accgtttgtg | 180 |
| tcgtggtttc atcctcggaa ccctcaaggg attttagcgg tggttacaat cattgccttt | 240 |
| gtgttgaaac gatacacgaa tgtgaaaata aaggcgaaaa tggcttaccg gaggaagttt | 300 |
| tggaggaata tgatgcggac ggctttgact tatgaggaat gggctcatgc tgctaagatg | 360 |
| ttagagaagg aaacaccaaa gatgaatgaa tctgatcttt atgatgaaga gttggttaag | 420 |
| aacaagcttc aggagcttcg tcatcgtcgc caagaaggct cacttagaga cattatgttt | 480 |
| tgtatgagag ctgatttggt gaggaatctc ggtaatatgt gtaattcgga gcttcataaa | 540 |
| ggtagacttc aggttcctag acatatcaaa gagtacattg atgaggtgtc tactcagttg | 600 |
| agaatggttt gtaactctga ttcagaggag ctttctttag aagagaagct ttcttttatg | 660 |
| catgaaacac ggcatgcctt tggtagaacg gctttgcttt tgagtggtgg ggcttctctt | 720 |
| ggtgcgtttc atgttggtgt ggttaggact ttggttgagc ataagctttt acctcgaata | 780 |
| attgctggtt ctagtgttgg atccatcatt tgtgctgttg tggcctcaag gtcttggcca | 840 |
| gaactacaga gtttctttga gaattctttg cattctttac agttctttga tcagctcgga | 900 |
| ggcgtgttct caatagtgaa acgggtaatg acacaagggg ctctacacga tatcagacag | 960 |

-continued

```
ttgcaatgta tgcttagaaa cctcacaagc aatctcacat tccaagaagc ttatgacatg   1020
acaggaagga ttctcgggat caccgtttgc tccccaagaa agcatgaacc tcctcggtgt   1080
cttaactatt tgacttcgcc tcatgtggtt atatggagcg cagtgactgc ttcttgtgct   1140
tttcctggtc tctttgaagc tcaagagcta atggctaaag atcgaagtgg agagatcgta   1200
ccgtatcatc caccttttcaa tttggatcca gaagtaggca ctaaatcatc atctggacgc   1260
cggtggagag atggtagttt ggaggttgat ttaccaatga tgcagcttaa aaaactgttc   1320
aatgtcaatc attttattgt gagccaagcc aatcctcaca ttgctccatt actgcgtcta   1380
aaggatttag ttcgagctta tggtggtaga ttcgcagcta agctcgcgca tctagtggag   1440
atggaggtca acatagatg caaccaggta ttagagctcg gttttcctct cggtggactc   1500
gcaaagcttt ttgctcagga gtgggaaggt gatgttacag ttgtaatgcc tgctactctt   1560
gctcagtact cgaagattat acaaaatccg actcatgtcg agcttcagaa agcggctaac   1620
caaggaagaa gatgcacttg ggagaagctc tcagccataa aatcaaactg cgggatcgag   1680
cttgcgcttg atgattctgt agctattctt aaccatatgc ggaggctcaa gaaaagtgcg   1740
gagagagccg ccactgccac gtcttcgtct catcacggat tggcttcaac caccagattc   1800
aatgcttcaa gaagaatccc atcttggaac gtccttgcca gagagaactc aacaggctca   1860
ctggatgatc tagtcactga caataacctc cacgcttctt cgggcaggaa tttaagcgac   1920
agtgaaacag agagcgtgga gttgagttct tggacaagaa ctggtggacc tttaatgaga   1980
acagcttctg ctaataagtt cattgatttt gttcagagtc ttgatatcga cattgcattg   2040
gtcagaggat ttagtagcag tcccaattct ccagcagttc ctcctggtgg ctcgtttact   2100
ccaagcccga gatccatagc ggctcattcg gatatcgaat caaacagcaa tagcaacaat   2160
cttggaacaa gcacttcaag cataacagtt actgaaggtg atcttctaca gcctgagaga   2220
acgagtaacg gatttgtgtt aaacgtcgtt aaaagagaga acttgggaat gccatcgatt   2280
gggaaccaaa atacagagtt accagagagt gtacagctcg atataccgga gaaggagatg   2340
gattgtagct ctgtatcaga acacgaagaa gatgataacg acaatgaaga agaacataac   2400
ggctcgagtc tggttactgt ttcttcagaa gattccggtt tacaagaacc ggtgtctggt   2460
agtgttatag atgcttag                                                  2478
```

<210> SEQ ID NO 13
<211> LENGTH: 2478
<212> TYPE: DNA
<213> ORGANISM: Arabidopsis thaliana

<400> SEQUENCE: 13

```
atggatataa gtaatgaggc tagtgtcgat cccttttcga ttggaccatc atctatcatg     60
ggtcgaacca ttgctttcag agtcttgttc tgtagatcaa tgtcacagct taggcgtgat    120
ctctttcggt tcttgttgca ttggtttctt agatttaagc tgaccgtttc accgtttgtg    180
tcgtggtttc atcctcggaa ccctcaaggg attttagcgg tggttacaat cattgccttt    240
gtgttgaaac gatacacgaa tgtgaaaata aaggcgaaaa tggcttaccg gaggaagttt    300
tggaggaata tgatgcggac ggctttgact tatgaggaat gggctcatgc tgctaagatg    360
ttagagaagg aaacaccaaa gatgaatgaa tctgatcttt atgatgaaga gttggttaag    420
aacaagcttc aggagcttcg tcatcgtcgc caagaaggct cacttagaga cattatgttt    480
tgtatgagag ctgatttggt gaggaatctc ggtaatatgt gtaattcgga gcttcataaa    540
ggtagacttc aggttcctag acatatcaaa gagtacattg atgaggtgtc tactcagttg    600
```

```
agaatggttt gtaactctga ttcagaggag ctttctttag aagagaagct ttcttttatg    660
catgaaacac ggcatgcctt tggtagaacg gctttgcttt tgagtggtgg ggcttctctt    720
ggtgcgtttc atgttggtgt ggttaggact ttggttgagc ataagctttt acctcgaata    780
attgctggtt ctagtgttgg atccatcatt tgtgctgttg tggcctcaag gtcttggcca    840
gaactacaga gtttctttga gaattctttg cattctttac agttctttga tcagctcgga    900
ggcgtgttct caatagtgaa acgggtaatg acacaagggg ctctacacga tatcagacag    960
ttgcaatgta tgcttagaaa cctcacaagc aatctcacat tccaagaagc ttatgacatg   1020
acaggaagga ttctcgggat caccgtttgc tccccaagaa agcatgaacc tcctcggtgt   1080
cttaactatt tgacttcgcc tcatgtggtt atatggagcg cagtgactgc ttcttgtgct   1140
tttcctggtc tctttgaagc tcaagagcta atggctaaag atcgaagtgg agagatcgta   1200
ccgtatcatc caccttttcaa tttggatcca gaagtaggca ctaaatcatc atctggacgc   1260
cggtggagag atggtagttt ggaggttgat ttaccaatga tgcagcttaa agaactgttc   1320
aatgtcaatc attttattgt gagccaagcc aatcctcaca ttgcttcatt actgcgtcta   1380
aaggatttag ttcgagctta tggtggtaga ttcgcagcta agctcgcgca tctagtggag   1440
atggaggtca aacatagatg caaccaggta ttagagctcg gttttcctct cggtggactc   1500
gcaaagcttt ttgctcagga gtgggaaggt gatgttacag ttgtaatgcc tgctactctt   1560
gctcagtact cgaagattat acaaaatccg actcatgtcg agcttcagaa agcggctaac   1620
caaggaagaa gatgcacttg ggagaagctc tcagccataa aatcaaactg cgggatcgag   1680
cttgcgcttg atgattctgt agctattctt aaccatatgc ggaggctcaa gaaaagtgcg   1740
gagagagccg ccactgccac gtcttcgtct catcacggat tggcttcaac caccagattc   1800
aatgcttcaa gaagaatccc atcttggaac gtccttgcca gagagaactc aacaggctca   1860
ctggatgatc tagtcactga caataacctc cacgcttctt cgggcaggaa tttaagcgac   1920
agtgaaacag agagcgtgga gttgagttct tggacaagaa ctggtggacc tttaatgaga   1980
acagcttctg ctaataagtt cattgatttt gttcagagtc ttgatatcga cattgcattg   2040
gtcagaggat ttagtagcag tcccaattct ccagcagttc tcctggtgg ctcgtttact   2100 ccaagcccga gatccatagc ggctcattcg gatatcgaat caaacagcaa tagcaacaat   2160 cttgaacaa gcacttcaag cataacagtt actgaaggtg atcttctaca gcctgagaga   2220
acgagtaacg gatttgtgtt aaacgtcgtt aaaagagaga acttgggaat gccatcgatt   2280
gggaaccaaa atacagagtt accagagagt gtacagctcg atataccgga gaaggagatg   2340
gattgtagct ctgtatcaga acacgaagaa gatgataacg acaatgaaga gaacataac   2400 ggctcgagtc tggttactgt ttcttcagaa gattccggtt tacaagaacc ggtgtctggt   2460
agtgttatag atgcttag                                                2478
```

<210> SEQ ID NO 14
<211> LENGTH: 367
<212> TYPE: DNA
<213> ORGANISM: Ricinus communis

<400> SEQUENCE: 14

```
aggttgattt accaatgatg caattgaagg aactgttcaa cgtcaatcac tttattgtga     60
gtcaggcaaa tcctcatatt gctccgttgt tgagaatgaa ggagtttgtg agagcttatg    120
gtggtaattt tgctgccaag cttgctcatc tcactgagat ggaagtaaag catagatgca    180
atcaggtact ggaacttggt tttccattag gaggacttgc caagcttttt gctcaagaat    240
```

```
gggagggcga tgtcactgtt gttatgcctg ccacagtgtc tcagtacttg aaaataattc    300
aaaatccaac tcacatggaa cttcaaaagg cagccaacca agggagaaga tgcacttggg    360
agaagct                                                              367
```

```
<210> SEQ ID NO 15
<211> LENGTH: 121
<212> TYPE: PRT
<213> ORGANISM: Ricinus communis

<400> SEQUENCE: 15
```

```
Val Asp Leu Pro Met Met Gln Leu Lys Glu Leu Phe Asn Val Asn His
  1               5                  10                  15

Phe Ile Val Ser Gln Ala Asn Pro His Ile Ala Pro Leu Leu Arg Met
             20                  25                  30

Lys Glu Phe Val Arg Ala Tyr Gly Gly Asn Phe Ala Ala Lys Leu Ala
         35                  40                  45

His Leu Thr Glu Met Glu Val Lys His Arg Cys Asn Gln Val Leu Glu
     50                  55                  60

Leu Gly Phe Pro Leu Gly Gly Leu Ala Lys Leu Phe Ala Gln Glu Trp
 65                  70                  75                  80

Glu Gly Asp Val Thr Val Val Met Pro Ala Thr Val Ser Gln Tyr Leu
                 85                  90                  95

Lys Ile Ile Gln Asn Pro Thr His Met Glu Leu Gln Lys Ala Ala Asn
            100                 105                 110

Gln Gly Arg Arg Cys Thr Trp Glu Lys
        115                 120
```

```
<210> SEQ ID NO 16
<211> LENGTH: 2406
<212> TYPE: DNA
<213> ORGANISM: Arabidopsis thaliana

<400> SEQUENCE: 16
```

```
atggatataa gcaacgaagc aggcgttgat gcgttctcaa ttataggacc cacgactata     60
atcggaagaa caattgccgt ccggatcttg ttctgcaact ccgtgtctat attcagacac    120
aaagttttca gaattctcaa attttttcctc agaggaggta gggttttact atcaccgttt   180
gtgtccttgc tacatcccag gaatccacaa gggatattag taatggtgac gacgatggcc    240
tttctgttga accgctacac aagcttaaaa gcaaaggctg agatggctta caggagaaaa    300
ttttggagga acatgatgag agctgcattg acatatgagg aatggtctca cgccgcaaag    360
atgctagata aagagactcc caaggtgaac gagacagatc tttttgatgt ggagctcgta    420
agtaataagc ttgatgaact taagcataga cgtcatgagg gctctcttag agacattatt    480
ttctgtatga gagctgatct tgtgagaaat ctcggtaata tgtgtaaccc tgagcttcac    540
aagggaaggc ttcacgtgcc gagactcatc aaagagtata tcgatgaggt ctctacacag    600
cttaggatgg tttgcgacat ggacactgaa gagctttctc tggaggagaa acttttctttt   660 atgcatgaga ccagacacgc gtatggaaga acagctctac ttctcagtgg aggagcttct    720 cttgggggctt ccatcttggg tgtggtcaag acgcttgtgg aacataagct attgccaaga    780
attatagctg gttcaagcgt ggggtctgta atgtgtgcgg ttgtggggac aaggtcatgg    840
cccgagttgc agagcttctt tgaagggtcc tggcatgctc tgcagttctt tgatcagatg    900
ggaggaattt tcactactgt gaagcgggtt atgactcaag cgcagtccaa tgagatccgg    960
catctgcaat ggaagttgag gaatctcacc aacaatctca cattccaaga agcttacgac   1020
```

```
ataacaggac ggattctagg gataacagtt tgttccctga ggaaacacga gccgcctaga  1080
tgtctcaatt atctgacttc gcctcatgtt gtgatatgga gtgcagtgac tgcatcttgt  1140
gctttcccag gtcttttcga agctcaagaa ctcatggcca agacagaac tggagagatt   1200
gttccttatc atccaccatt taacttagat cctgaagagg gctcagcatc agttcggcgc  1260
tggagggacg gtagtttgga gatggactta ccgatgatac aactcaaaga gcttttcaat  1320
gtcaaccatt tcattgtcag tcaagccaac cctcacatag caccctttctt gaggatgaag  1380
gagtttgtga gagcttgtgg aggtcgattt gcagcaaagc tcgcgcaact cgcggagatg  1440
gaagtgaagc atagatgtaa tcaagtacta gaactcgggc ttcctctaag agaagtagct  1500
tcactatttg ctcaagaatg ggaaggcgat gtcacaattg tcatgccagc tacttttttct 1560
cagtacttga agatcataca aaatccaagc aatgtagaga ttcaaaaggc agcaaatcaa  1620
ggaaggagat gcacctggga aaaactagca gtaatcaaag caaacttcgg gatcgaacta  1680
gcactcgacg agtgcgtcac cgttcttaac cacatgcgcc gccttaaacg cagcgcagaa  1740
agagccgctg ctttctccgc catctcttcc tctccaccat ctaaacatct tttggccgga  1800
accaatagat tcaacgcctc caaaagaatc ccttcctgga attgtatagc tcgtcagaac  1860
tcctccggat ccgtcgatga tgatgtccta gctgaagctt cacggttgta ccagcatatc  1920
gtggttggat ctgggaggaa tagtaatcga accagtaact taagccatac ctatgacgca  1980
ggaagcgaat gtgattctcc agaagctgaa gattggacta gatctggcgg accattgatg  2040
aggaccaatt ctgctcagat gttcactgac tacgtccaga atctcgacgc cgttgatccg  2100
gaacagatta gagcttcgga gaacgattcg attgtagctg cttcgtcgtc ttctcatagc  2160
atcactgtca cggaaggcga ttatcttcag acgggaagaa cacacaatgg atttgtgttg  2220
aatctcgtta gaggagagaa tttgaggatg aattcagagc cggaagatag ccaaaacgaa  2280
agtgaaattc cggagactcc ggaaagcgtg caacttgatt cgccggaaaa ggacattatt  2340
gacggagaga gctcggcgtc ggaagacgga gacgctcagg cgaatctaat ccatgaccat  2400
gagtaa                                                             2406
```

<210> SEQ ID NO 17
<211> LENGTH: 801
<212> TYPE: PRT
<213> ORGANISM: Arabidopsis thaliana

<400> SEQUENCE: 17

```
Met Asp Ile Ser Asn Glu Ala Gly Val Asp Ala Phe Ser Ile Ile Gly
1               5                   10                  15

Pro Thr Thr Ile Ile Gly Arg Thr Ile Ala Val Arg Ile Leu Phe Cys
            20                  25                  30

Asn Ser Val Ser Ile Phe Arg His Lys Val Phe Arg Ile Leu Lys Phe
        35                  40                  45

Phe Leu Arg Gly Gly Arg Val Leu Leu Ser Pro Phe Val Ser Leu Leu
    50                  55                  60

His Pro Arg Asn Pro Gln Gly Ile Leu Val Met Val Thr Thr Met Ala
65                  70                  75                  80

Phe Leu Leu Asn Arg Tyr Thr Ser Leu Lys Ala Lys Ala Glu Met Ala
                85                  90                  95

Tyr Arg Arg Lys Phe Trp Arg Asn Met Met Arg Ala Ala Leu Thr Tyr
            100                 105                 110

Glu Glu Trp Ser His Ala Ala Lys Met Leu Asp Lys Glu Thr Pro Lys
        115                 120                 125
```

-continued

Val Asn Glu Thr Asp Leu Phe Asp Val Glu Leu Val Ser Asn Lys Leu
            130                 135                 140

Asp Glu Leu Lys His Arg Arg His Glu Gly Ser Leu Arg Asp Ile Ile
145                 150                 155                 160

Phe Cys Met Arg Ala Asp Leu Val Arg Asn Leu Gly Asn Met Cys Asn
                165                 170                 175

Pro Glu Leu His Lys Gly Arg Leu His Val Pro Arg Leu Ile Lys Glu
            180                 185                 190

Tyr Ile Asp Glu Val Ser Thr Gln Leu Arg Met Val Cys Asp Met Asp
                195                 200                 205

Thr Glu Glu Leu Ser Leu Glu Glu Lys Leu Ser Phe Met His Glu Thr
210                 215                 220

Arg His Ala Tyr Gly Arg Thr Ala Leu Leu Ser Gly Gly Ala Ser
225                 230                 235                 240

Leu Gly Ala Phe His Leu Gly Val Val Lys Thr Leu Val Glu His Lys
                245                 250                 255

Leu Leu Pro Arg Ile Ile Ala Gly Ser Ser Val Gly Ser Val Met Cys
            260                 265                 270

Ala Val Val Gly Thr Arg Ser Trp Pro Glu Leu Gln Ser Phe Phe Glu
            275                 280                 285

Gly Ser Trp His Ala Leu Gln Phe Phe Asp Gln Met Gly Gly Ile Phe
            290                 295                 300

Thr Thr Val Lys Arg Val Met Thr Gln Gly Ala Val His Glu Ile Arg
305                 310                 315                 320

His Leu Gln Trp Lys Leu Arg Asn Leu Thr Asn Asn Leu Thr Phe Gln
                325                 330                 335

Glu Ala Tyr Asp Ile Thr Gly Arg Ile Leu Gly Ile Thr Val Cys Ser
                340                 345                 350

Leu Arg Lys His Glu Pro Pro Arg Cys Leu Asn Tyr Leu Thr Ser Pro
            355                 360                 365

His Val Val Ile Trp Ser Ala Val Thr Ala Ser Cys Ala Phe Pro Gly
            370                 375                 380

Leu Phe Glu Ala Gln Glu Leu Met Ala Lys Asp Arg Thr Gly Glu Ile
385                 390                 395                 400

Val Pro Tyr His Pro Pro Phe Asn Leu Asp Pro Glu Glu Gly Ser Ala
                405                 410                 415

Ser Val Arg Arg Trp Arg Asp Gly Ser Leu Glu Met Asp Leu Pro Met
                420                 425                 430

Ile Gln Leu Lys Glu Leu Phe Asn Val Asn His Phe Ile Val Ser Gln
            435                 440                 445

Ala Asn Pro His Ile Ala Pro Phe Leu Arg Met Lys Glu Phe Val Arg
450                 455                 460

Ala Cys Gly Gly Arg Phe Ala Ala Lys Leu Ala Gln Leu Ala Glu Met
465                 470                 475                 480

Glu Val Lys His Arg Cys Asn Gln Val Leu Glu Leu Gly Leu Pro Leu
                485                 490                 495

Arg Glu Val Ala Ser Leu Phe Ala Gln Glu Trp Glu Gly Asp Val Thr
                500                 505                 510

Ile Val Met Pro Ala Thr Phe Ser Gln Tyr Leu Lys Ile Ile Gln Asn
                515                 520                 525

Pro Ser Asn Val Glu Ile Gln Lys Ala Ala Asn Gln Gly Arg Arg Cys
            530                 535                 540

Thr Trp Glu Lys Leu Ala Val Ile Lys Ala Asn Phe Gly Ile Glu Leu
545                 550                 555                 560

Ala Leu Asp Glu Cys Val Thr Val Leu Asn His Met Arg Arg Leu Lys
            565                 570                 575

Arg Ser Ala Glu Arg Ala Ala Phe Ser Ala Ile Ser Ser Ser Pro
        580                 585                 590

Pro Ser Lys His Leu Leu Ala Gly Thr Asn Arg Phe Asn Ala Ser Lys
            595                 600                 605

Arg Ile Pro Ser Trp Asn Cys Ile Ala Arg Gln Asn Ser Ser Gly Ser
610                 615                 620

Val Asp Asp Val Leu Ala Glu Ala Ser Arg Leu Tyr Gln His Ile
625                 630                 635                 640

Val Val Gly Ser Gly Arg Asn Ser Asn Arg Thr Ser Asn Leu Ser His
            645                 650                 655

Thr Tyr Asp Ala Gly Ser Glu Cys Asp Ser Pro Glu Ala Glu Asp Trp
            660                 665                 670

Thr Arg Ser Gly Gly Pro Leu Met Arg Thr Asn Ser Ala Gln Met Phe
        675                 680                 685

Thr Asp Tyr Val Gln Asn Leu Asp Ala Val Asp Pro Glu Gln Ile Arg
690                 695                 700

Ala Ser Glu Asn Asp Ser Ile Val Ala Ala Ser Ser Ser His Ser
705                 710                 715                 720

Ile Thr Val Thr Glu Gly Asp Tyr Leu Gln Thr Gly Arg Thr His Asn
            725                 730                 735

Gly Phe Val Leu Asn Leu Val Arg Gly Glu Asn Leu Arg Met Asn Ser
                740                 745                 750

Glu Pro Glu Asp Ser Gln Asn Glu Ser Glu Ile Pro Glu Thr Pro Glu
        755                 760                 765

Ser Val Gln Leu Asp Ser Pro Glu Lys Asp Ile Ile Asp Gly Glu Ser
    770                 775                 780

Ser Ala Ser Glu Asp Gly Asp Ala Gln Ala Asn Leu Ile His Asp His
785                 790                 795                 800

Glu

<210> SEQ ID NO 18
<211> LENGTH: 1110
<212> TYPE: DNA
<213> ORGANISM: Arabidopsis thaliana

<400> SEQUENCE: 18
atggcgatgt ctctccgttc cactccattc atctctctcc gtacgagaaa aagctttaac      60
ctttctccga gaattctcgc ccttaggtta tcatgctgct ctggtgggtc ttctcaaaat     120
cagaactttt ctacagattc cgagaacaag agatcattcg ctgttgccac cggtgagctt     180
ttcatcggaa tcgcgtcgag gcttttgaag agttctaatc aaaagacgcc gccgattgat     240
gatggtgata aatagctag tgtaattgag gatgagattg agccagcgat gatatgggaa     300
caaagggtta agatgttga agcggagaaa gagaggagag tcattacaag tcctgggttt     360
agtttctctg ctgctggtct tttgtttcct tatcatcttg gagttgctca gttgcttatt     420
gaaaagggtt acataaagga aactactcct ttagcaggat cttctgctgg tgctatagtc     480
tgtgctgtga taacctcagg agctactatg cgagaagccc ttgaagctac taaggaactt     540
gcttatgatt gtcgacgcaa tggcactgct ttccgtcttg gggctgtcct tagagaatcc     600
atggagaggt tactgcccga tgatattcac attaggtcca acgggagaat tcgtgttgcc     660
atcactcaag tgttttggag acctagaggt cttctagtgg atcagttcga ctccaaaagc     720

```
gacttgatag atgcagtttt cacatcttct tttattccag gatatcttgc accaaggcct    780
gcaacaatgt tccgtaatcg actttgtgtt gatggaggct tgacattgtt tatgccacca    840
acagctgctg ctaaaacagt tcgagtttgt gcttttccg ctagtaactt caaactaaag    900
ggtattgaga tctgcccaga ttgcaaccct ttaaacagag caacatctag acaactattg    960
aattgggcac ttgagccagc agaggacgag gtgttggaga ggctgtttga gttaggatac    1020
gcagatgcag ctcatgggc tgagatgaat ccagttgagg gattggtcta tgacgatact    1080
cctacagctc aagagattcc tactagctaa                                     1110
```

<210> SEQ ID NO 19
<211> LENGTH: 369
<212> TYPE: PRT
<213> ORGANISM: Arabidopsis thaliana
<400> SEQUENCE: 19

```
Met Ala Met Ser Leu Arg Ser Thr Pro Phe Ile Ser Leu Arg Thr Arg
1               5                   10                  15

Lys Ser Phe Asn Leu Ser Pro Arg Ile Leu Ala Leu Arg Leu Ser Cys
            20                  25                  30

Cys Ser Gly Gly Ser Ser Gln Asn Gln Asn Phe Ser Thr Asp Ser Glu
        35                  40                  45

Asn Lys Arg Ser Phe Ala Val Ala Thr Gly Glu Leu Phe Ile Gly Ile
    50                  55                  60

Ala Ser Arg Leu Leu Lys Ser Ser Asn Gln Lys Thr Pro Pro Ile Asp
65                  70                  75                  80

Asp Gly Asp Arg Ile Ala Ser Val Ile Glu Asp Ile Glu Pro Ala
                85                  90                  95

Met Ile Trp Glu Gln Arg Val Lys Asp Val Glu Ala Glu Lys Glu Arg
            100                 105                 110

Arg Val Ile Thr Ser Pro Gly Phe Ser Phe Ser Ala Ala Gly Leu Leu
        115                 120                 125

Phe Pro Tyr His Leu Gly Val Ala Gln Leu Leu Ile Glu Lys Gly Tyr
    130                 135                 140

Ile Lys Glu Thr Thr Pro Leu Ala Gly Ser Ser Ala Gly Ala Ile Val
145                 150                 155                 160

Cys Ala Val Ile Thr Ser Gly Ala Thr Met Arg Glu Ala Leu Glu Ala
                165                 170                 175

Thr Lys Glu Leu Ala Tyr Asp Cys Arg Arg Asn Gly Thr Ala Phe Arg
            180                 185                 190

Leu Gly Ala Val Leu Arg Glu Ser Met Glu Arg Leu Leu Pro Asp Asp
        195                 200                 205

Ile His Ile Arg Ser Asn Gly Arg Ile Arg Val Ala Ile Thr Gln Val
    210                 215                 220

Phe Trp Arg Pro Arg Gly Leu Leu Val Asp Gln Phe Asp Ser Lys Ser
225                 230                 235                 240

Asp Leu Ile Asp Ala Val Phe Thr Ser Ser Phe Ile Pro Gly Tyr Leu
                245                 250                 255

Ala Pro Arg Pro Ala Thr Met Phe Arg Asn Arg Leu Cys Val Asp Gly
            260                 265                 270

Gly Leu Thr Leu Phe Met Pro Pro Thr Ala Ala Lys Thr Val Arg
        275                 280                 285

Val Cys Ala Phe Ser Ala Ser Asn Phe Lys Leu Lys Gly Ile Glu Ile
    290                 295                 300

Cys Pro Asp Cys Asn Pro Leu Asn Arg Ala Thr Ser Arg Gln Leu Leu
```

```
                            305                 310                 315                 320
        Asn Trp Ala Leu Glu Pro Ala Glu Asp Glu Val Leu Glu Arg Leu Phe
                        325                 330                 335

Glu Leu Gly Tyr Ala Asp Ala Ala Thr Trp Ala Glu Met Asn Pro Val
                        340                 345                 350

Glu Gly Leu Val Tyr Asp Asp Thr Pro Thr Ala Gln Glu Ile Pro Thr
                        355                 360                 365

Ser

<210> SEQ ID NO 20
<211> LENGTH: 148
<212> TYPE: PRT
<213> ORGANISM: Solanum tuberosum

<400> SEQUENCE: 20

Phe His Val Gly Val Val Arg Thr Leu Val Glu His Lys Leu Leu Pro
        1               5                   10                  15

Arg Ile Ile Ala Gly Ser Ser Val Gly Ser Ile Ile Cys Ala Val Val
                        20                  25                  30

Ala Ser Arg Ser Trp Pro Glu Leu Gln Ser Phe Phe Glu Asn Ser Leu
                    35                  40                  45

His Ser Leu Gln Phe Phe Asp Gln Leu Gly Gly Val Phe Ser Ile Val
                50                  55                  60

Lys Arg Val Met Thr Gln Gly Ala Leu His Asp Ile Arg Gln Leu Gln
        65                  70                  75                  80

Cys Met Leu Arg Asn Leu Thr Ser Asn Leu Thr Phe Gln Glu Ala Tyr
                        85                  90                  95

Asp Met Thr Gly Arg Ile Leu Gly Ile Thr Val Cys Ser Pro Arg Lys
                    100                 105                 110

His Glu Pro Pro Arg Cys Leu Asn Tyr Leu Thr Ser Pro His Val Val
                115                 120                 125

Ile Trp Ser Ala Val Thr Ala Ser Cys Ala Phe Pro Gly Leu Phe Glu
            130                 135                 140

Ala Gln Glu Leu
        145

<210> SEQ ID NO 21
<211> LENGTH: 362
<212> TYPE: PRT
<213> ORGANISM: Saccharomyces cerevisiae

<400> SEQUENCE: 21

Thr Tyr Gln Met Trp Cys Gln Gln Ala Ser Val Val Asp Glu Ile Thr
        1               5                   10                  15

Gly Ala Asn Leu Trp Arg Arg Asn Phe Phe Ser Arg Arg Tyr Asp Phe
                        20                  25                  30

Asn Ser Val Ile Glu Gln Tyr Ser Ile Leu Glu Asn Met Leu Arg Glu
                    35                  40                  45

Glu Lys Tyr Asp Val Val Lys Glu Lys Phe Ser Thr Thr Gly Pro Cys
                50                  55                  60

Met Leu Arg Asn Phe Ala Gly Ile Gly Asp Lys Lys Leu Phe Thr Lys
        65                  70                  75                  80

Ser Leu Met Gly Thr Lys Leu Leu Ile Glu Gln Tyr Leu Thr Arg Ile
                        85                  90                  95

Leu Glu Gly Leu Asp Ile Leu Asn Asn Gln Thr Leu Thr Pro Thr Ser
                    100                 105                 110
```

```
Phe Phe Gln Arg Cys Lys Leu Ser Leu Gly Thr Thr Ala Leu Ile Leu
            115                 120                 125

Gln Gly Gly Ser Leu Phe Gly Leu Phe His Leu Gly Val Ile Arg Gly
        130                 135                 140

Leu Leu Leu Gln Asp Leu Met Pro Asn Ile Ile Ser Gly Ser Ser Met
145                 150                 155                 160

Gly Ala Cys Val Ala Ser Leu Phe Gly Cys Leu Ser Asn Glu Gln Leu
                165                 170                 175

Lys Gln Leu Leu Thr Asp Asp Asn Leu Leu Asn Ile Ile Lys Asn Asp
            180                 185                 190

Val Asp Leu Leu Lys Ser Cys Gly Tyr Gly Asn Leu Glu Gln His Leu
            195                 200                 205

Asn Leu Gly Thr Leu Ile Gln Asn Leu Ile His His Gly Tyr Ser Gln
            210                 215                 220

Asp Val Tyr Leu Phe Ile Arg Phe Val Met Lys Tyr Ile Val Lys Glu
225                 230                 235                 240

Lys Thr Phe Glu Glu Val Tyr Gln Ile Thr Gly Lys Val Phe Asn Ile
                245                 250                 255

Val Ile His Pro Thr Asp Lys Ser Cys Pro Asn Leu Leu Asn Tyr Val
                260                 265                 270

Thr Thr Pro Asn Val Leu Ile Lys Ser Ala Ile Glu Cys Ser Leu Gly
            275                 280                 285

Ser Gly Val Ile Ser Glu Asp Thr Ser Leu Leu Cys Lys Asn Leu Glu
            290                 295                 300

Asn Glu Ile Glu Pro Phe Leu Asn Ile Asn Lys Asn Lys Gln Val Lys
305                 310                 315                 320

Phe Leu Thr Pro Glu Asn Ala Asn Asn Pro Ser Ile Thr Glu Ser Pro
                325                 330                 335

Tyr Thr Arg Leu Thr Glu Leu Phe Asn Val Asn Asn Phe Ile Val Ser
            340                 345                 350

Leu Ala Arg Pro Tyr Leu Ala Pro Leu Val
            355                 360
```